US006997882B1

(12) United States Patent
Parker et al.

(10) Patent No.: US 6,997,882 B1
(45) Date of Patent: Feb. 14, 2006

(54) 6-DOF SUBJECT-MONITORING DEVICE AND METHOD

(75) Inventors: B. Eugene Parker, Charlottesville, VA (US); Brendan M. Fabeny, Charlottesville, VA (US); Edward C. Larson, Severn, MD (US); Jeffrey F. Monaco, Charlottesville, VA (US)

(73) Assignee: Barron Associates, Inc., Charlottesville, VA (US)

( * ) Notice: Subject to any disclaimer, the term of this patent is extended or adjusted under 35 U.S.C. 154(b) by 0 days.

(21) Appl. No.: 10/328,214

(22) Filed: Dec. 21, 2002

Related U.S. Application Data

(60) Provisional application No. 60/343,396, filed on Dec. 21, 2001.

(51) Int. Cl.
*A61B 5/08* (2006.01)
(52) U.S. Cl. .................. 600/534; 600/301; 600/595
(58) Field of Classification Search ........... 600/300, 600/301, 529–543, 481, 508, 531, 595; 73/23.3; 607/6; 482/8, 148, 901, 909
See application file for complete search history.

(56) References Cited

U.S. PATENT DOCUMENTS

| | | | | |
|---|---|---|---|---|
| 3,998,106 | A | | 12/1976 | William |
| 4,038,536 | A | * | 7/1977 | Feintuch .................... 708/322 |
| 4,267,845 | A | * | 5/1981 | Robertson et al. .......... 600/534 |
| 4,444,205 | A | * | 4/1984 | Jackson ..................... 600/595 |
| 5,309,922 | A | * | 5/1994 | Schechter et al. ......... 600/534 |
| 5,341,811 | A | * | 8/1994 | Cano .......................... 600/508 |
| 5,573,013 | A | | 11/1996 | Conlan |
| 5,592,401 | A | * | 1/1997 | Kramer ..................... 702/153 |
| 5,615,132 | A | * | 3/1997 | Horton et al. ................ 703/7 |
| 5,670,944 | A | * | 9/1997 | Myllymaki ............. 340/573.1 |
| 5,701,894 | A | | 12/1997 | Cherry et al. |
| 5,749,372 | A | | 5/1998 | Allen et al. |
| 5,851,193 | A | * | 12/1998 | Arikka et al. ............... 600/595 |
| 5,855,550 | A | * | 1/1999 | Lai et al. .................... 600/300 |
| 5,919,149 | A | * | 7/1999 | Allum ........................ 600/595 |
| 6,064,910 | A | * | 5/2000 | Andersson et al. ........... 607/20 |
| 6,102,856 | A | | 8/2000 | Groff et al. |
| 6,128,955 | A | | 10/2000 | Mimura |
| 6,132,337 | A | | 10/2000 | Krupka et al. |
| 6,160,478 | A | * | 12/2000 | Jacobsen et al. ....... 340/539.12 |
| 6,175,108 | B1 | | 1/2001 | Jones et al. |
| 6,192,756 | B1 | | 2/2001 | Kikuchi et al. |
| 6,215,403 | B1 | | 4/2001 | Chan et al. |
| 6,305,221 | B1 | * | 10/2001 | Hutchings .................... 73/488 |
| 6,306,088 | B1 | | 10/2001 | Krausman et al. |
| 6,307,481 | B1 | * | 10/2001 | Lehrman et al. ............ 340/669 |
| 6,384,728 | B1 | | 5/2002 | Kanor et al. |
| 6,397,677 | B1 | | 6/2002 | Kinsley et al. |
| 6,402,968 | B1 | | 6/2002 | Yazdi et al. |
| 6,409,687 | B1 | * | 6/2002 | Foxlin ....................... 600/595 |
| 6,422,076 | B1 | | 7/2002 | Prokofiev et al. |
| 6,427,534 | B1 | | 8/2002 | D'Amico |

(Continued)

OTHER PUBLICATIONS

D.G. Ward—Generalized Networks For Complex Function Modeling 1994 IEEE Systems, Man & Cybernetics Conference, Oct. 2-5 San Antonio, TX.

*Primary Examiner*—Max F. Hindenburg
*Assistant Examiner*—Patricia Mallari
(74) *Attorney, Agent, or Firm*—Denis O'Brien

(57) ABSTRACT

The present invention comprises novel methods and devices for monitoring a subject by acquiring reliable and accurate 6-DOF data regarding the subject, and by using those data to obtain information about the subject's movements in three-dimensional space. Information regarding the subject's movements is, optionally, combined with information regarding the subject's physiological status so that comprehensive knowledge regarding the subject may be acquired by those monitoring the subject.

15 Claims, 9 Drawing Sheets

U.S. PATENT DOCUMENTS

| | | |
|---|---|---|
| 6,433,690 B1 | 8/2002 | Petelenz et al. |
| 6,436,052 B1 | 8/2002 | Nikolic et al. |
| 6,493,652 B1 * | 12/2002 | Ohlenbusch et al. ........ 702/160 |
| 6,498,994 B1 * | 12/2002 | Vock et al. .................... 73/488 |
| 6,605,044 B1 * | 8/2003 | Bimbaum ................... 600/500 |
| 6,605,046 B1 * | 8/2003 | Del Mar ..................... 600/507 |
| 6,611,783 B1 * | 8/2003 | Kelly et al. ................. 702/150 |
| 6,702,755 B1 * | 3/2004 | Stasz et al. ................. 600/534 |

* cited by examiner

6-DOF SUBJECT-MONITORING DEVICE AND METHOD

RELATED APPLICATIONS

Reference is made to Provisional Application No. 60/343,396, filed on Dec. 21, 2001, with respect to which priority is claimed pursuant to 35 U.S.C. § 119(e).

FEDERALLY SPONSORED RESEARCH

The U.S. Government has a paid-up license in this invention and the right in limited circumstances to require the patent owner to license to others on reasonable terms as provided by the terms of the following grants:
Department of Education grant ED-00-PO3741;
Department of Education grant ED-01-CO-0123;
National Institute on Aging grant 1R43AG18667-01A1.

BACKGROUND OF THE INVENTION

1. Field of the Invention

This invention relates to devices and methods for monitoring and measuring the movements and the physiological status of living subjects, particularly ambulatory subjects.

2. The Prior Art

Subject-monitoring systems comprise devices and methods that collect data about various aspects of a living subject. Such systems routinely process and communicate thse data to provide useful and usable information about the subject. Two aspects of subject-monitoring systems are of particular interest with respect to the present invention: accelerometry and monitoring physiological status.

A. Accelerometry

Accelerometry is the practice of measuring the acceleration of a body with respect to a reference-frame, which reference-frame may comprise one, two, or three-dimensions depending on the application. Accelerometry plays a vital role in a number of fields, including navigation, transportation, seismology, air-bag technology and aerospace engineering; consequently, the field of accelerometry has benefitted from significant and impressive advances in devices and methods used for measuring acceleration.

The most widely accepted system of describing the movement of a subject in three-dimensional space is to describe the motion with respect to three mutually orthogonal axes—x,y, and z, referred to as Cartesian axes. For each of the three axes, it is possible for the subject to undergo two types of movement: 1) along the axis (translational movement), or 2) about or around the axis (rotational movement). Given two types of movement occurring with respect to three axes, it will be appreciated that in order to fully describe the movement of a subject in three-dimensional space, one must simultaneously consider the motion in all "six degrees of freedom" (6-DOF), in the parlance of the art. If one also wishes precisely to analyze the movement of the subject's limbs and extremities in addition to the movement of the subject as a whole, then the movement of each limb or extremity of interest must be independently subjected to 6-DOF analysis. Obviously, such efforts depend heavily on devices that are capable of sensing acceleration: accelerometers.

Numerous types of accelerometers are available, such as those characterized as solid state (U.S. Pat. No. 6,402,968); piezo-electric (U.S. Pat. No. 6,397,677); magnetic (U.S. Pat. No. 6,427,534); mercury-based (U.S. Pat. No. 3,998,106); fibre optic (U.S. Pat. No. 6,175,108); and pendulum (U.S. Pat. No. 6,422,076). In addition to accelerometers, gyroscopes of various descriptions can be used to measure angular velocities (see U.S. Pat. No. 6,192,756 to Kikuchi et al.).

Accelerometers measure linear or translational acceleration with respect to an axis, referred to as "the axis of measurement" of the accelerometer. The standard accelerometer measures acceleration along one axis of measurement. Such an accelerometer is referred to as "uniaxial." There are also devices in which multiple accelerometers are aggregated in a common package, which device may then have two (biaxial) or three (triaxial) axes of measurement. As used herein, the term "accelerometer module" refers to an accelerometer device having one or more axes of measurement.

The technology for acquiring 6-DOF data with respect to rigid bodies is employed in a variety of fields, such as automotive engineering and aerospace control systems. In the accelerometry of inert, rigid bodies, the accelerometer modules can be permanently affixed to the object by adhesives, welding, screws, etc., and hence the axes of measurement are predetermined and fixed. This significantly simplifies the computations and techniques for obtaining 6-DOF data. An example is U.S. Pat. No. 6,128,955, granted to Mimura, which teaches how to obtain 6-DOF data with respect to a rigid body such as a vehicle. Mimura's approach is, essentially, to solder three uniaxial accelerometer modules to a rigid plate, oriented so that they sense motion occurring along the vertical, or z, axis. Three additional uniaxial accelerometer modules are attached to the same rigid plate oriented such that they sense motion in arbitrary directions in the x-y plane, which plane is orthogonal to the z-axis. The acceleration data thus collected are then processed to provide 6-DOF data about the movements of the vehicle.

The present invention exploits and improves upon existing accelerometry technology as a means of enhancing subject-monitoring by obtaining and utilizing 6-DOF data. Prior to the present invention, the advantages of 6-DOF accelerometry have not been extended to subject-monitoring; nevertheless, physiology and medicine have benefitted from the availability of uniaxial (1-DOF), biaxial (2-DOF), and triaxial (3-DOF), accelerometer modules. In addition, 4-DOF measurements have been described. For example, U.S. Pat. No. 6,436,052 issued to Nikolic et al., discloses the use of two 2-axis solid state accelerometer modules attached to a subject to monitor and measure 4-DOF acceleration in the x-y plane. From the raw data so obtained it is possible, according to the computational methods disclosed by Nikolic, to derive approximate rates of oxygen consumption, and, hence, the amount of work done by the subject. Such applications of accelerometer modules to monitor the activity of a subject are fairly common, and additional examples may be found in U.S. Pat. Nos. 6,306,088; 5,573,013; and 6,307,481.

Pedometers, a sub-set of this art-field, generally employ one or more uniaxial accelerometer modules or motion detectors attached to one or more of a subject's body-segments. By employing such pedometers, information regarding steps taken, cadence, distance travelled, and energy expenditure may be obtained. The invention of Takenaka, disclosed in U.S. Pat. No. 6,254,513, is a representative example of how elementary accelerometer-based pedometers can be employed in the art of measuring human movement. Because existing pedometer devices do not utilize 6-DOF technology, they do not provide information regarding rotational movements and other three-dimensional aspects of gait that must be determined in order fully to analyze a subject's gait.

B. Physiological Monitoring

Predictions of high rates of increase in the numbers of elderly persons requiring care in the coming decades have become quite common. For instance, Petenlenz et al (U.S. Pat. No. 6,433,690) have cited statistics predicting the total number of falls that elderly persons will experience over the coming decades. Such statistics indicate that the amount of care the elderly will require over the next forty years is increasing at an alarming rate. Although the areas to which the present invention can be applied extend well beyond the care of the elderly, the field of patient and elderly care is an especially fertile source of relevant art because the present invention relates to devices and means for obtaining information related to the motion, position, and orientation of a subject in three-dimensional space, in combination with information indicative of the subject's physiological status—information that is often sought by those caring for aged persons.

Although the field is far too large to inventory here, a representative example of devices and methods that are used to monitor the physiological status of patients is U.S. Pat. No. 6,102,856, issued to Groff et al, who disclose a monitoring-system that collects, analyzes and transmits information related to the vital signs of a patient. Another such representative device is disclosed by U.S. Pat. No. 6,215,403 to Chan et al. which discloses a complex of sensors for monitoring a variety of physiological parameters simultaneously. Typically, such devices utilize readily-available sensors that detect and measure physiological parameters and functions such as body temperature, heart rate, cardiac electrical activity, and respiratory function.

The relevant prior art teaches how to use such sensors to collect physiological data, process the data, and transmit them to a monitoring device, or activate some sort of alarm when the parameters being measured indicate an abnormal and/or detrimental condition, such as a precipitous fall in heart rate. When such physiological monitoring systems are combined with accelerometers, one may simultaneously monitor a subject's physiological status and his/her movements, orientation, and position in three-dimensional space. Cherry et al. (U.S. Pat. No. 5,701,894) discloses one such invention combining elementary accelerometry and physiological monitoring.

As discussed above, existing subject-monitoring devices and methods do not have a 6-DOF capability; hence, they can provide, at best, only an incomplete analysis of a subject's movement in three-dimensional space. Nevertheless, such devices can roughly determine, for example, whether the subject is horizontal or vertical, or whether he/she is changing from vertical to horizontal. When such information is combined with data regarding physiological status, a useful impression, even if somewhat imprecise, emerges as to the subject's overall condition. This technology would benefit significantly by 6-DOF measurement capabilities.

BRIEF SUMMARY OF THE INVENTION

1. Overview of the Invention

The present invention represents a novel, useful, and non-obvious approach to subject-monitoring systems because it provides a device and methodology for collecting and analyzing 6-DOF data relevant to the subject's acceleration, velocity, position, and orientation. In addition, it provides a device and methodology for combining 6-DOF data with physiological data indicative of the subject's physiological status. When such activity and physiological data are combined and synchronized, a large amount of very useful information about the subject can be obtained. For example, information about whether some aspect of the subject's physiology has caused a change in the subject's position, such as a hypotensive event causing a fall. Or, conversely, information about whether and to what extent the subject's movements have altered his physiology, such as the effect of exercise on heart rate. These are just two of the many ways movement and physiological information can be synchronized in order to monitor the physical and physiological activity of subjects.

2. Uses of the Invention

The utility of the present invention will be obvious to one who considers the breadth of its potential applications, which include, by way of example: 1) monitoring the timing, frequency, intensity, and duration of activity in subjects, such as for sports studies or obesity epidemiological studies; 2) monitoring activity and vital signs in soldiers, firefighters, or emergency personnel via continuous transmission or remote wireless interrogation; 3) monitoring instantaneous or cumulative caloric expenditure; 4) monitoring heart rate as a function of activity; 5) providing 6-DOF gait-analysis with corrective feedback for disabled subjects or athletes; 6) monitoring physiological and physical activity in sleep studies, including sleep apnea and sudden infant death syndrome; 7) providing 6-DOF data for medical diagnosis and assessment related to orthopedic problems: 8) monitoring geriatric patients in order to respond to falls; 9) reconstructing and analyzing falls after the fact, using 6-DOF data in a way analogous to the way aircraft black-box data are used; 10) monitoring the level of patient care by care-givers; and 11) carrying out industrial ergonomic studies combining motion analysis with physiological data such as electromyography. While the use of less than 6-DOF accelerometry in many of the foregoing applications is well known, the list is representative of the types of applications that will benefit significantly from the 6-DOF measurement capabilities of the present invention.

3. Shortcomings of Prior Art Overcome by the Invention

There are substantial technological hurdles to the application of 6-DOF techniques to subject-monitoring that the prior art has not overcome. For instance, in order to generate 6-DOF data describing the movements of a body, at least six motion sensors for acquiring the raw motion data must be attached to the body-segment. When working with an inanimate, rigid body, the accelerometer modules can be carefully aligned with respect to one another and secured to the body so that they maintain a fixed position with respect to the coordinate axes of the rigid body. But in a living subject, the accelerometer modules cannot be welded, soldered, or glued to the body-segment, consequently they invariably move with respect to one another—movement that is very hard or impossible to control. This means that considerable additional computational effort is required in processing the raw data from the accelerometer modules in order to compensate for imprecise a priori alignment and for movement of accelerometer modules with respect to the anatomical reference-frame. And in situations in which 6-DOF data are to be collected from multiple body-segments simultaneously, the total streams of data that must be processed is 6n, where n is the number of segments monitored. If the goal of the subject-monitoring exercise is to display information reflecting the subject's movements in real time, then all of the 6-DOF data must be collected and converted to useful information in a very short time span. If that information is to be integrated with information regarding the physiological status of the subject, then the task of processing large amounts of information very quickly becomes even more daunting. These problems, not heretofore resolved by the prior art, are overcome by the present invention.

Another major shortcoming of the prior art that is overcome by the present invention is that the prior art does not teach how to apply accelerometry to the direct measurement of respiratory function. Prior art approaches to directly determining respiratory movements are essentially limited to the use of sensors that measure chest expansion, such as an EPM Systems Model No. 1310 or a ProTech Model No. 1461, which both employ pizeoelectric transducers in a stretchable belt placed around the subject's thorax. Until the present invention, it has not been possible to derive rate and depth of respiration from whole-body accelerometry data collected, for example, from accelerometer modules attached to the subject's chest or waist.

4. Objects of the Invention

The present invention overcomes the foregoing shortcomings of the prior art by attaining the following objects:

A To provide a device capable of acquiring 6-DOF data in a living subject;

B. To provide a method for processing 6-DOF data collected from subjects so as to derive comprehensive information about the subject's movements, position, and orientation in three-dimensional space, including information descriptive of gait & ambulation, falls or near-falls, energy expenditure;

C. To provide a device and method for processing accelerometry data to derive information about the subject's respiratory movements;

D. To provide a device and method for storing 6-DOF data and/or information about the subject's movements derived from those data;

E. To provide a device and method for transmitting 6-DOF data collected from subjects (and/or information derived from those data) to remote processing, storage, or monitoring devices;

F. To provide a method for using 6-DOF data collected from subjects to re-construct a living subject's movements, including, as required, integrating the movement information with the subject's physiological data over the some Δt, for after-the-fact analysis and/or diagnostic procedures;

G. To provide a device and method of synchronizing 6-DOF data with physiological data collected from subjects and for displaying the synchronized information;

H. To provide a 6-DOF device, including, as required, sensors for collecting physiological data, that is small enough to be worn comfortably for long periods of time by either ambulatory or bed-ridden subjects;

I. To provide a device and method for continuously measuring and storing 6-DOF data and reconstructing translational and rotational accelerations with respect to the x, y, and z axes of an inertial and/or anatomical reference-frame, along with translational and angular velocity and position/orientation information;

J. To provide a device and method for collecting 6-DOF data in subjects, which by itself or in combination with physiological data, particularly heart rate, is used to derive information about the subject's energy expenditure;

K. To provide a method of calibrating accelerometer modules attached to a subject in order to compensate for the movements of the modules with respect to an anatomical and/or inertial reference-frame.

BRIEF DESCRIPTION OF THE SEVERAL VIEWS OF THE DRAWINGS

1. The Drawings.

The objects, features and advantages of the invention will become apparent from the following DETAILED DESCRIPTION OF THE INVENTION taken in connection with the accompanying drawings, in which.

2. TABLE OF FIGURE REFERENCE NUMBERS

Figure 1:
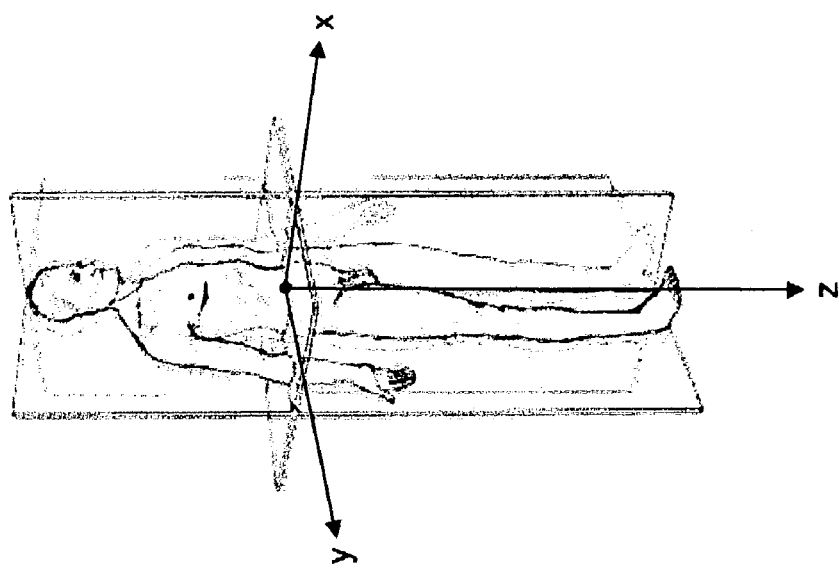
FIG. 1 represents a human subject with Cartesian reference-frame superimposed.

| Ref # | Description | Ref # | Description |
|---|---|---|---|
| 100 | Cartesian reference-frame | 102 | Subject |
| 104 | x, y (transverse) plane | 106 | x, z (sagittal) plane |
| 108 | y, z (frontal) plane | 200 | Transverse body section |
| 202 | Anterior aspect | 204 | Posterior aspect |
| 206 | 1st accelerometer module | 208 | 2nd accelerometer module |
| 210 | 3rd accelerometer module | 212 | Anatomical reference-frame |
| 214 | Inertial reference-frame | 300 | Belt-style local unit |
| 302 | Belt | 304 | Microprocessor unit |
| 306 | Battery | 402 | HR electrode #1 |
| 404 | HR electrode #2 | 406 | HR electrode #3 |
| 408 | LCD | 500 | 1 piece component strip |
| 502 | Flexible PCB | 504 | Battery |
| 506 | 1st accelerometer module | 508 | Microprocessor |
| 510 | 2nd accelerometer module | 512 | Temperature sensor |
| 514 | 3rd accelerometer module | 516 | Component strip on cover |
| 518 | Snap | 520 | Cover |
| 522 | Velcro fasteners | 600 | Local unit |
| 602 | Remote unit | 604 | Accelerometer array |
| 606 | Physiological sensor array | 608 | Data bus |
| 610 | Local processor | 612 | Local memory |
| 614 | Local display | 616 | Local transceiver |
| 618 | Remote memory | 620 | Remote processor |
| 622 | Remote transceiver | 624 | Remote display |
| 700 | Pelvis cross-section | 702 | Posterior aspect |
| 704 | Anterior aspect | 706 | 1st accelerometer module |
| 708 | 2nd accelerometer module | 710 | 3rd accelerometer module |
| 712 | 4th accelerometer module | 714 | 1st posterior vector |

-continued

2. TABLE OF FIGURE REFERENCE NUMBERS

| Ref # | Description | Ref # | Description |
| --- | --- | --- | --- |
| 716 | 2nd posterior vector | 718 | 3rd posterior vector |
| 720 | 4th posterior vector | 722 | 1st anterior vector |
| 724 | 2nd anterior vector | 726 | 3rd anterior vector |
| 728 | 4th anterior vector | 730 | 1st resulting vector |
| 732 | 2nd resulting vector | 734 | 3rd resulting vector |
| 736 | 4th resulting vector | 800 | Adaptive noise-cancelling device |
| 802 | Input for sum of 1st & 2nd resulting vector | 804 | Input for sum of 3rd & 4th resulting vector |
| 806 | Output of estimated respiratory movement | 808 | Summing junction |
| 810 | Filter | | |

DETAILED DESCRIPTION OF THE INVENTION

1. Definitions

Whenever the terms listed below are used in the specification, claims, and abstract of this application, or any amendments made thereto, they shall be understood to have the meanings here set forth:

A. subject—a living individual of any species, including (but not exclusively) *Homo sapiens*.

B. body-segment—any one of the following parts of a subject's body: head, neck, thorax, abdomen, pelvis, upper arm, forearm, thigh, calf, ankle, hand, or foot, or their equivalents in non-human species.

C. accelerometer—any means for collecting raw data relevant to the translational and/or rotational acceleration of a body: including, by way of example solid-state accelerometers, piezoelectric accelerometers, magnetic accelerometers, fibre optic accelerometers, pendulum accelerometers, and gyroscopes.

D. movement—a change in position or orientation of a subject, or any body-segment of a subject. The term encompasses acceleration, velocity, rotation, and translation or any other term denoting or indicating a change in position or orientation.

E. 6-DOF data—aggregated data that 1) are derived from raw data obtained from a plurality of accelerometer modules, and that 2) are representative of the movements of a subject or body-segment in three-dimensional space, which is to say, the rotational and translational movements of the subject or body-segment along or around each axis of a Cartesian reference-frame. The term includes binary representations of such data, and information obtained by processing such data, such as, by way of example, a) integrating and/or differentiating the data with respect to time to derive velocities, positions, and orientations, and b) converting the data to a form or format that is comprehensible to humans when displayed.

F. comprehensible to humans—refers to data or information configured or formatted so as to be directly intelligible to humans, if properly displayed. Information or data that are comprehensible to humans include, by way of example, text, digits, numbers, graphical displays, light pulses and LED displays, audible signals, words and cues.

2. The Preferred Embodiment of the Invention

A Structure: Device for Collecting and Processing 6-DOF Data [FIGS. 1–3]

Referring first to FIG. 1, a standard convention for superimposing three planes of a Cartesian reference-frame 100 upon a human subject 102 may be appreciated. A horizontal plane (transverse plane) 104 is defined by an x and y axes. One vertical plane (frontal) 108 is defined by the y-axis and a z-axis. A second vertical plane (sagittal) 106 is defined by the x and z axes. By the convention, the z-axis extends in a superior-inferior direction (i.e., vertically downwards, for an upright subject); the y-axis is orthogonal to the z-axis and extends in the medio-lateral direction (from the subject's left to right); and the x-axis is orthogonal to both the z and y axes and extends in the posterior-anterior direction (from the subject's back to front). However, this convention is entirely arbitrary, and any orientation of a Cartesian reference-frame with respect to the subject may be employed in order to monitor the movements of the subject in three-dimensional space.

It will also be appreciated from FIG. 1 that there are two types of movement with respect to each of the three axes: translational movement of the body to-and-fro along an axis, or any combination of axes, and rotational movement of the body around an axis, or any combination of axes. With respect to whole-body movements, any combination of the two types of motion with respect to the chosen reference-frame can be monitored by attaching a device capable of collecting 6-DOF data to the pelvic area of the subject. Attachment to any part of the torso would be acceptable from a technical point of view, assuming that the necessary computational compensations are applied; however, having the accelerometer modules near the center of mass has significant advantages, as discussed below. In addition, pelvic attachment is more comfortable for subjects.

If one wishes to monitor the activity of one or more body-segments in addition to the pelvis, or as an alternative to the pelvis, then a device capable of collecting raw 6-DOF data can be attached to the body-segments of interest. Where the simultaneous movements of multiple body-segments are to be analyzed, a separate Cartesian reference-frame may be applied to each body-segment, or body-segments may be analyzed with respect to a single, fixed reference-frame.

Figure 2:
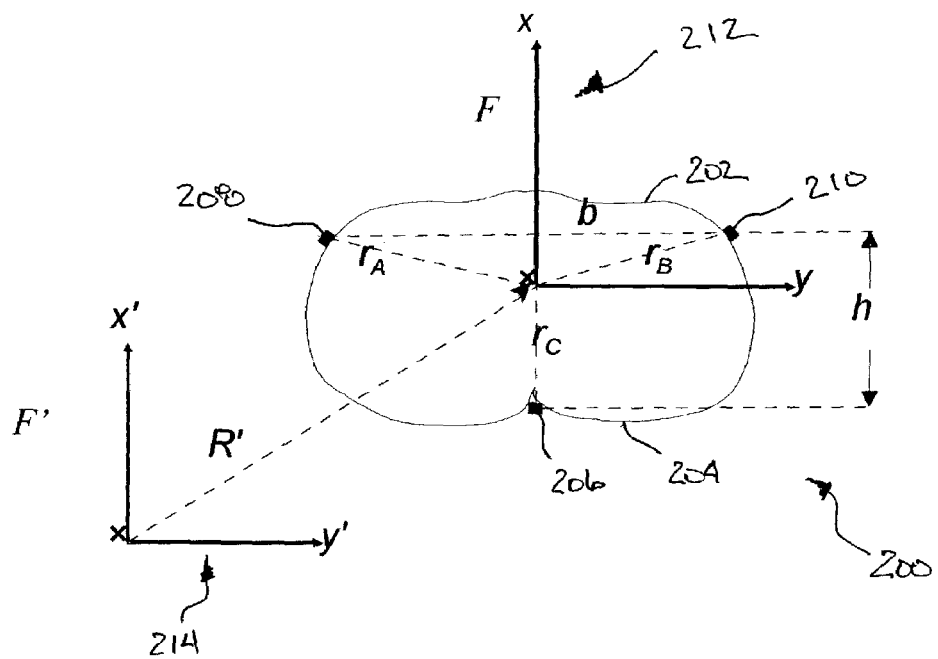
FIG. 2 represents a transverse section of a subject's pelvis with anatomical reference-frame and inertial reference-frame.

The foregoing will be more readily understood by referring to FIG. 2, which represents a cross-section 200 of a human torso at approximately the level of the L5/S1 vertebral junction. The figure is provided to indicate the arrangement of three biaxial accelerometer modules according to the best known mode of practicing the invention. Other necessary or optional components of the device, discussed below, are omitted from FIG. 2 for clarity of description. In the transverse cross-section, the anterior aspect 202 and posterior aspect 204 are distinguished. Superimposed upon the cross-section is a reference-frame 212. (The z-axis is not evident because it is projecting into the plane of the page as indicated by the "x" symbol.) Such a reference-frame is referred to herein as an "anatomical reference frame" because it maintains its orientation with respect to the body-segment, the pelvis in this example. By comparison, reference-frame 214 retains its orientation with respect to the earth, hence it is referred to herein as an "inertial reference-frame." It is the problem of determining the relative motions of various body-segments of the subject in the anatomical reference-frame relative to the inertial reference-frame that is resolved by our invention.

An array of accelerometer modules that produce acceleration signals is attached to the subject. On the posterior surface of the subject, at or near the midline, is attached one biaxial accelerometer module 206. A second biaxial accelerometer module 208 is attached to the subject's left side, approximately adjacent the left iliac crest. A third biaxial accelerometer module 210 is attached to the subject's right side, approximately adjacent the right iliac crest. With this array and arrangement of three accelerometer modules on the subject's waist, it is possible, by the techniques described below, to acquire six discrete and substantially simultaneous acceleration signals, which are processed to yield 6-DOF data describing the movements of the subject's pelvis.

The accelerometer arrangement shown of FIG. 2 is but one of many configurations in which an array of accelerometer modules can be attached to a subject in order to acquire raw data from which 6-DOF data are derived. For instance, six uniaxial accelerometer modules deployed at optimal positions on the subject would produce equivalent results. More precision may be obtained by redundancy of measurement, for instance, by having an array of eight or ten biaxial accelerometer modules, but because six is the maximum number of degrees of freedom that exist, a complete complement of 6-DOF data can be acquired by three biaxial accelerometer modules in the configuration shown.

Depending on the specific accelerometer devices employed, the output accelerometer signals may be analog or digital representations of the acceleration in the respective axes of measurements. These signals are processed by a microprocessor unit (not shown in FIG. 2) and stored, transmitted, and converted into an informational format that can be displayed. The computational steps in processing the raw data are described below.

Figure 3:
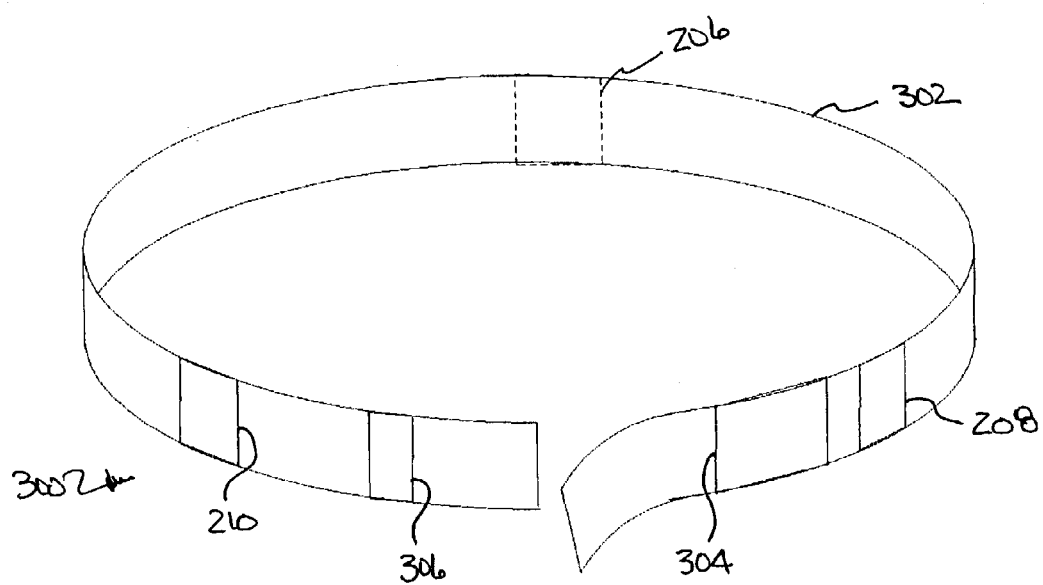
FIG. 3 represents a basic local unit and attachment means for acquiring 6-DOF data.

In FIG. 3 is shown a basic waistband configuration that incorporates the minimum components required for 6-DOF data collection according to the preferred embodiment. The purpose of FIG. 3 is to illustrate the basic system required to obtain 6-DOF data from a subject; consequently, the device represented by FIG. 3 does not, for instance, include any display components or any components for transmitting or receiving data. These components are discussed below.

Waistband 302 is a flexible band for attaching the components to the subject. The means of fastening the ends of the belt together may be a buckle, Velcro™ hook and loop fasteners, clips, snaps, or other means commonly used in the art. Alternatively, the waistband may be sufficiently expandable that the waistband can be made as a single, closed piece that can be put over the subject's head or feet and slid into place.

A first biaxial accelerometer module 206 is mounted on the belt such that when the belt is attached to the subject, the accelerometer will be positioned posteriorly, approximately over the vertebral column. Biaxial accelerometer module 208 and biaxial accelerometer 210 are positioned on the belt such that when the belt is attached to the subject they will be positioned on the left and right anterior iliac crests, respectively.

An example of a type of accelerometer module that has been used successfully is Analog Devices' model ADXL210, which is a biaxial micro-machined module on a monolithic integrated circuit (IC) having a full-scale range of ±10g. This module is capable of detecting both dynamic and static (i.e. gravity) accelerations. The two axes of measurement are oriented perpendicular to each other within the circuit. Each sensing axis has associated with it a duty-cycle modulated (DCM) output that is linearly proportional to the sensed acceleration. A duty cycle equal to 0.5 represents zero acceleration; a duty cycle greater than 0.5 implies a positive acceleration, and a value less than 0.5 implies a negative acceleration. To digitize the six DCM outputs, the six microprocessor timers are used, obviating the need to use microprocessor A/D converters for this purpose. If additional accelerometer modules are used (e.g., for deriving respiration), a microprocessor having a sufficient number of counters may be used or the DCM outputs can be lowpass filtered and fed to the extra microprocessor A/D converter inputs for digitization. These modules are mounted on small printed circuit boards, together with signal conditioning components, as described below. They are small enough to be worn by a subject without discomfort or interference with the subject's activities.

As an alternative (or addition) to accelerometer modules of the type just described, it is possible, and under some circumstances expedient, to employ gyroscopes to obtain raw data regarding rotational movements. For example, three uniaxial accelerometer modules can be combined with three rate gyroscopes to gather the data required to produce 6-DOF movement analysis. For example, Analog Devices' gyroscopes model ADXRS150 and ADRXS300 can be used for this purpose.

The microprocessor unit 304 is shown attached to the belt adjacent accelerometer 208; however, the position of the microprocessor unit relative to the accelerometer modules or to the subject is not critical. The term "microprocessor unit" includes a processing unit, timers, display, and on-board memory for storing processor instructions, results of computational steps, variables, and data. Placing the microprocessor unit on the anterior aspect of the subject, as shown in FIG. 3, is particularly convenient if it includes an on-board display means, as described below. The microprocessor unit is in communication with the accelerometer modules by means of a data bus.

An example of an appropriate microprocessor is model # H8S/2329F produced by Hitachi Semiconductors. This processor has 36 internal interrupts, 7 external interrupts, and an interrupt controller, which collectively provide a mechanism for precise software control. Internal peripherals such as timers and serial communications interrupt normal program flow when requesting to be serviced. The interrupt controller prioritizes these interrupts, which determines when a peripheral will be serviced. The processor's internal timer sets an interrupt at precise intervals (e.g. 0.01 seconds for a 100 Hz sample rate). With each interrupt, an interrupt service routine functions to sample the six accelerometer channels, described below. The H8S/2329F processor is equipped with six 16-bit timer/counters and eight 10-bit single-ended A/D converters, which are also used in processing the outputs from various physiological sensors. In addition, the processor provides a direct memory access (DMA) controller, a bus controller, a 2-channel digital-to-analog (D/A) converter, and two high-speed serial communication controllers (one of which is used to communicate with a PC to upload raw data). The processor has several power-saving features, such as "sleep mode", which can be used even between sampling instants to conserve power.

The H8S/2329F also includes 384 KB of nonvolatile Flash-RAM (program memory) and 32 KB RAM (scratchpad memory). This amount of operating memory is sufficient to store embedded programs and provide space for the necessary run-time variables required to carry out the processing chores. Using a microcontroller with on-chip memory reduces the system chip count, leading to a smaller package and lower power requirements. An 8 KB off-chip Flash-RAM is used to archive data in the present embodiment.

A power source 306 is also attached to the belt. A power bus delivers power to all of the components. The components can operate on a 3.3 Vdc power supply, and a 3.7 Vdc battery rated at 920 milliamp-hours is used (Ultralife UBP563450) in the present embodiment. Such batteries are available as rectangular and cylindrical cells, and are well known in the art. As discussed above, the microprocessor monitors the power source and will shut down the system or alert the user if power falls below acceptable levels.

C. Structure: Attachment Means, and Components for Collecting, Processing, Storing, Transmitting, and Displaying the Physiological Data—(FIGS. 4 & 5)

Figure 4:
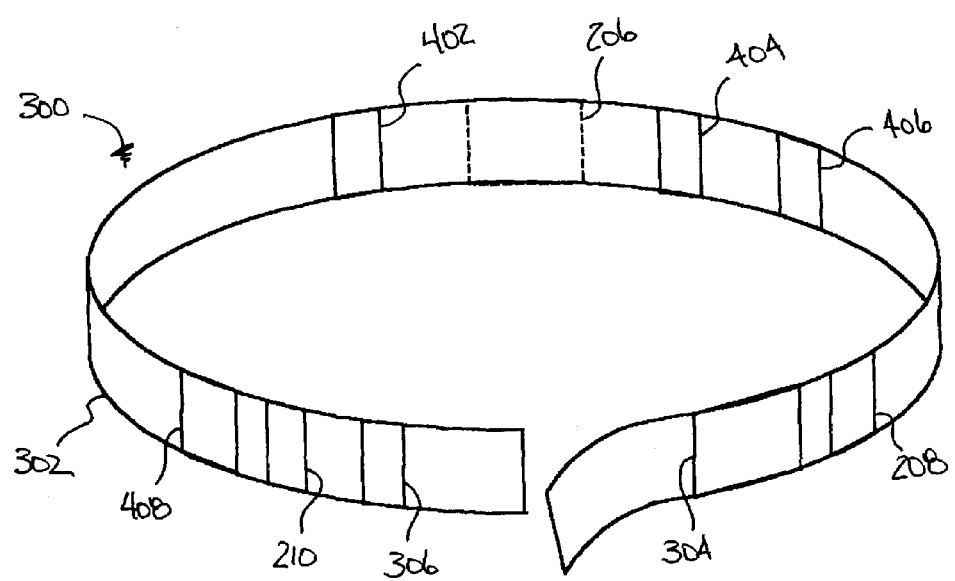
FIG. 4 represents a local unit and attachment means for acquiring 6-DOF data and physiological data.
Figure 5:
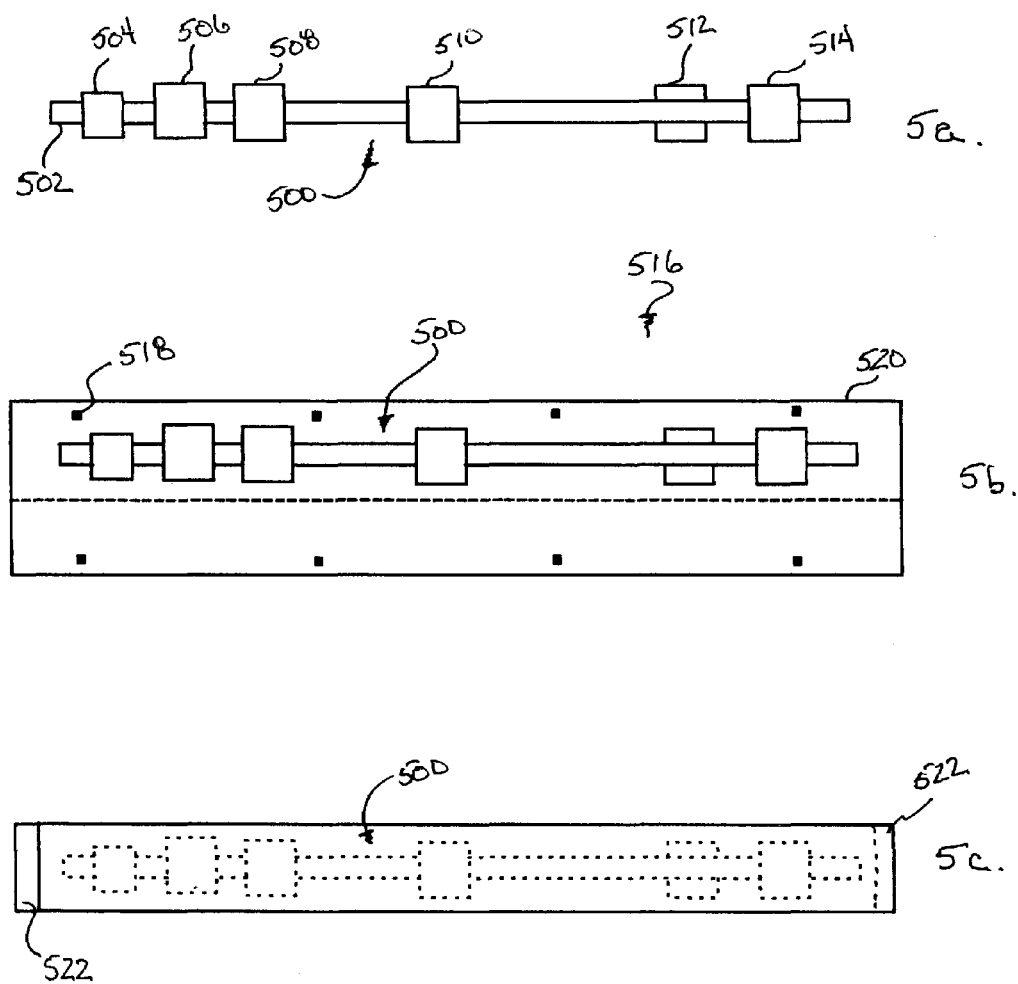
FIG. 5a represents a component mounting strip.
FIG. 5b represents component mounting strip being enclosed in band.
FIG. 5c represents component mounting strip enclosed in band.

FIG. 4. shows a belt-device for collecting 6-DOF data and physiological data simultaneously. The basic belt is as described in FIG. 3. The three biaxial accelerometer modules 206, 208, and 210 are attached to the belt for collecting the accelerometry data that are converted to 6-DOF data by microprocessor unit 304. Battery 306 supplies power to all components by means of a power bus (not shown). In the example of FIG. 4, heart rate (HR) data are the physiological data being collected simultaneously with 6-DOF data. The HR electrodes 404 and 406 collect the data and HR electrode 402 acts as a reference. The data from the HR electrodes are carried to the microprocessor unit 304. In addition, a liquid crystalline display ("LCD") 408 is provided as a local display unit. This display is useful for displaying information about the device, such as low battery levels, or data processed by the microprocessor, such as heart rate and/or energy expenditure. Alternatively or additionally, LEDs can be used to indicate various system states and conditions. It will be noted that the HR electrodes shown in FIG. 4 face inwards so that the electrodes maintain contact with the subject's skin, whereas other components of the system are located outside of the inner-most layer of the belt.

Other physiological sensors and/or transducers can be used in addition to or as alternatives to HR electrodes. Examples include sensors that collect: body temperature data, blood $O_2$ partial pressure data, blood $CO_2$ partial pressure data, respiration rate data, respiration depth data, micturition data, and skin conductance data. Micturition data include various measures of ambient humidity or the presence of moisture. These data can be used to alert care-givers of bed-wetting events or to record duration of wet bed-clothing in order to evaluate the level of patient care.

FIGS. 5a–5c show a preferred embodiment of the construction and attachment means for the local unit of the present invention. In FIG. 5a is shown a component mounting strip, which is a flexible printed circuit board (PCB) 502 upon which various components are connected and/or mounted. For example, the components may be discrete, rigid PCBs that attach to the flexible PCB band via solder pads. Alternatively, the components may be mounted directly on the flexible PCB.

Embedded within the PCB are buses for data and power (not shown). The components in this example include three biaxial accelerometer modules 506, 510, and 514 for collecting the raw accelerometry data that will be converted to 6-DOF data, a battery 504, a microprocessor unit 508, and a temperature sensor 512 that can monitor the subject. It is noted that the temperature sensor is given here as but one example of the type of physiological sensor that can be fruitfully combined with the 6-DOF device. The flexible PCB with its components is one example of what is referred to hereinafter as a "local unit" 500.

The entire local unit is sealed with a moisture resistant material, such as a conformal coating, so that it thus comprises a single, water-proof component that can be easily wiped clean or disinfected.

In FIG. 5b is shown the data recording unit laid upon a band 520 made of suitable material, such as cotton cloth, or a non-woven material. The band has attached to it a plurality of snaps 518 positioned so that when the band is folded at approximately its longitudinal midline, the snaps engage, thereby securing the data recording unit inside the folded band, as shown in FIG. 5c. The ends of the folded band have Velcro™ fastening strips so that the band, with the data recording unit inside, can be easily attached to the subject. Buckles, fasteners, clips, hooks, and snaps represent other means of securing the ends of the band.

It will be noted that in the example given here the temperature sensor faces the subject's skin. Other physiological sensors, such as micturition sensors, may not require direct skin contact. In situations where sensors must contact the skin, the band 520 may have windows at the appropriate locations so that the sensors are not occluded by the band. Such sensors may also be located on the inner-most layer of the band so as to contact the skin.

In addition to components of the system that are attached to the subject during monitoring, there are also components of the system that remain remote from the subject. Such remote components include a remote processor, remote memory, and remote display. Because the output from the microprocessor is in standard digital format, it can be easily transmitted or transferred to the remote processor as described below. The remote processor can be anything from a PALM device to a supercomputer, so long as it is capable of being programmed to process the data. A desktop or laptop PC is adequate for most applications. The next section discloses the functional relationship between local and remote units.

D. Operation: Information and Data Flow—[FIG. 6]

Figure 6:
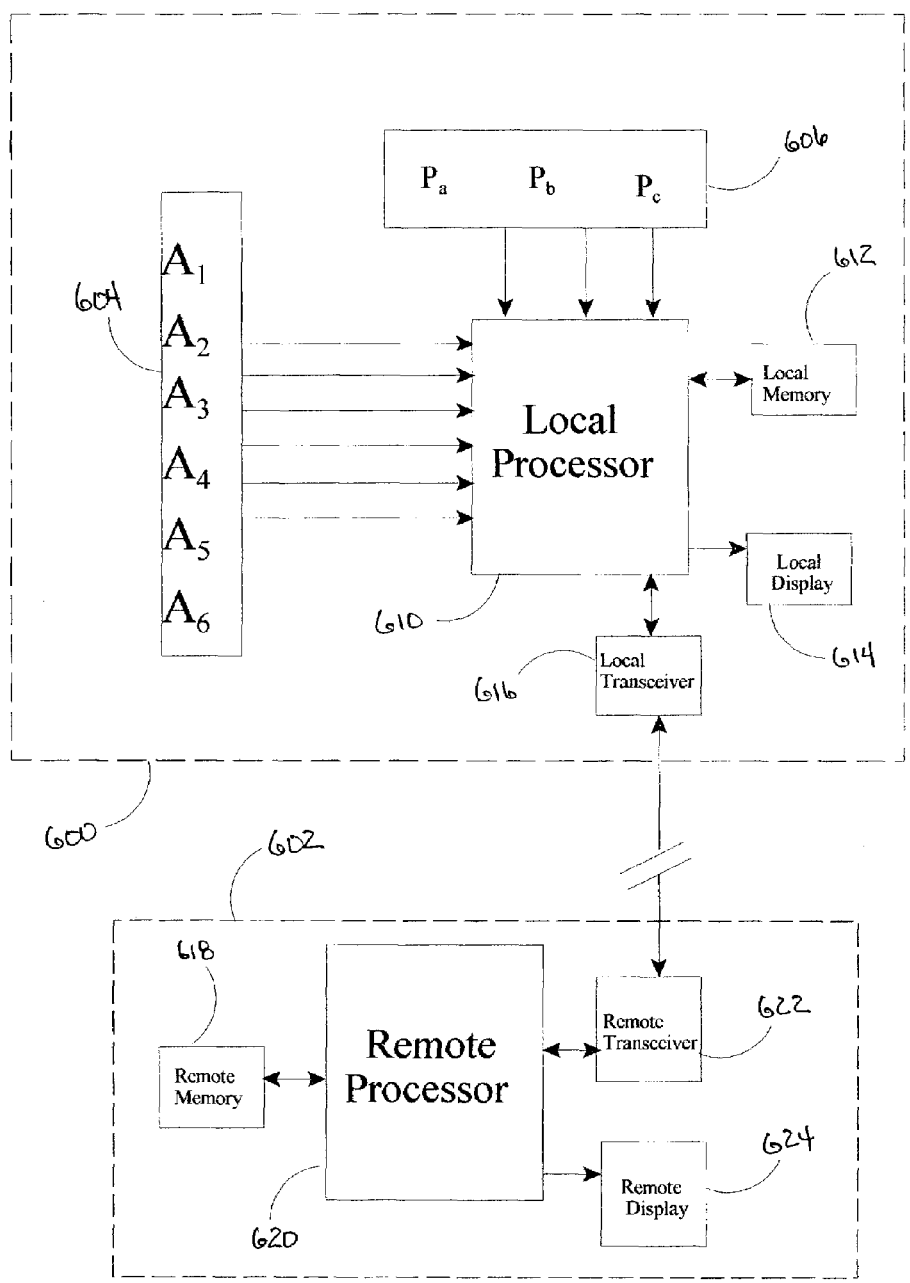
FIG. 6 is a block diagram showing the relationship of the components in a local unit and remote unit.

Referring to FIG. 6, the flow of data and information between the various components of the preferred embodiment may be appreciated. FIG. 6 is not meant to signify any specific grouping of sensors or modules, nor any specific sequence of steps. Such variables are determined on an ad hoc basis depending on the application.

Various types of data processing, display, and storage functions and devices are allocated between one or more local units 600, which comprise those components physically attached to the subject(s), and one or more remote units 602, which comprise those components of the system not attached to the subject. Although FIG. 6, for reasons of clarity, shows only one local unit and one remote unit, systems comprising a plurality of local and/or remote units are anticipated as being within the scope of the invention. For instance, in a hospital or battleground setting, one remote unit may receive data from and transmit data to many subjects, each of which wears a local unit. Alternatively, a local unit may communicate to a plurality of remote units. Such network systems are well known and easily implemented by those of ordinary skill in the art.

Data and information regarding movements and physiological status move between the local and remote units through a data transfer device which, in the preferred embodiment, comprises a local transceiver 616 in communication with a remote transceiver 622. The term data transfer device is here used in its broadest sense. It incorporates both wire-based, wireless, and combined wire/wireless means of transmitting, uploading, and/or downloading data. For instance, data stored in the 6 MB off-chip Flash-RAM of the local unit and physically transferred to a remote unit device capable of downloading those data represents an obvious means of transferring the 6-DOF data, in which case transceivers 616 and 622 comprise, or are supplemented by, memory read/write devices. In the preferred embodiment wireless transmission is used, employing Bluetooth wireless protocols and technology, well known to those skilled in the art. To implement the wireless communications, Ericsson's RCM 104001 Bluetooth Multichip Modules are used as the transceivers.

During the monitoring period, accelerometer signals are produced by an array of accelerometer modules 604. In the present embodiment array 604 is composed of three biaxial modules producing the required six accelerometer signals.

Accelerometer signals from the accelerometer modules represent the accelerations of the body-segment relative to each of the x, y, and z-axis of the anatomical reference-frame. These signals are transmitted to the local processor 610. Optionally, one or more physiological sensors 606 may send raw physiological data to the local processor. By providing a means to combine physiological data with 6-DOF data, the invention embodies very powerful subject-monitoring capabilities. The types of physiological data that may be acquired by the physiological sensors 606 include: heart rate data, body temperature data, transcutaneous blood $O_2$ partial pressure data, transcutaneous blood $CO_2$ partial pressure data, respiration rate data, respiration depth data, micturition data, and skin conductance data, as discussed above.

Local processor 610 converts the acceleration signals to digitized form, including 6-DOF data representing the movements of the body-segment with respect to the inertial reference-frame. Local processor also performs computational operations as dictated by the specific application at hand. The computational operations are described in detail below. Processor instructions for carrying out computations are held in local memory and/or can be transmitted to the local unit by the remote unit.

Local memory 612 comprises various storage units required to hold data, program instructions, variables, and results, as disclosed above. The memory may be fixed within the local unit, or it may be physically removable, such as readily available flash cards. Although the 6-DOF data produced by processing the accelerometry data can be quite voluminous, methods for exploiting memory are well known to those skilled in the art.

Local display 614 is intended to provide the user with limited information about the status of the local unit, or limited data output, for instance an LCD display of heart rate, or an audible signal that a threshold heart rate has been reached. The display takes the form of LEDs, LCDs, or audible signal generator, depending upon the objectives of the user. Information derived wholly or partly from the 6-DOF data (e.g., energy expenditure) may be displayed locally or transmitted to the remote unit for further processing, storage, and/or display.

Remote unit 602 comprises those components not physically attached to the subject. Remote processor 620 receives data from the local unit by means of the local and remote transceivers, as described above. The received data may be further processed before being sent to storage at remote memory 618, or before being sent to remote display 624 for displaying the movement information and/or the physiological information obtained during the monitoring period in a format comprehensible to humans.

In the present embodiment, much of the computational work is performed by the remote processor. This includes, by way of example, 1) conversion of the 6-DOF data to information descriptive of subject and body-segment movements, positions, and orientations; 2) conversion of physiological data into information descriptive of the subject's physiological status; 3) synchronization of the physiological and accelerometry data and information; 4) producing graphical representations of the subject's movements; 5) reconstructing complex sequences of movements, such as falls or athletic motions, 6) calculating estimates of energy expenditure; 7) performing gait analyses.

Given the disclosures here made, one skilled in computer programming can, without undue experimentation, produce acceptable software for implementing the steps of the invention and for exploiting the 6-DOF data acquired by the methods and devices of the invention. We have used the Hitachi Embedded Workshop (Ver. 1.1 a) to produce the instructions embedded in the local processor, and Visual Basic and MATLAB to produce software utilized by the remote processor; however, any readily available language and compiler may be used. Design features such as having the remote unit interrogate the local unit for data lying within specified ranges, or having the remote unit alter the program flow of the local unit will be obvious and easily implemented by those having ordinary skill in the art.

Remote memory 618 includes various devices for achieving data, such as CDs, DVDs, floppy disks, magnetic tapes, and flash memory cards. Remote memory also includes operational memory for storing program instructions, variables, intermediate values, and results of computations done by the remote processor.

The output of information in a format comprehensible to humans, as provided by remote display 624, has the capability of being significantly more sophisticated than that provided by local display 614. For instance, in a nursing home application, the information displayed includes patient identification, location, and physiological status in addition to motion and position information derived from the 6-DOF data. Alternatively, or additionally, by accessing the 6-DOF data acquired by the local unit, the remote unit is capable of producing and displaying animated reconstructions of the subject's movements using a "virtual pelvis" animation. When synchronized with physiological data, also acquired by the local unit, the remote unit can display time-referenced causal relationships, such as hypotensive events preceding falls. Once the methods and devices of the present invention for acquiring 6-DOF data in living subjects are implemented, many ways to exploit such data will be obvious to those of ordinary skill in the art.

E. Operation: Deriving Information Regarding the Movements, Positions, and Orientations of a Body-Segment and a Subject from 6-DOF Data—[FIGS. 2 & 3]

This section discloses the manner in which the preferred embodiment of the invention derives 6-DOF data from the accelerometer signals in order to obtain information regarding angular and translational accelerations, angular and rotational velocities, translational positions, and angular orientations of a body-segment during a monitoring period. In this example, a pelvis 200, as depicted in FIG. 2, is used as the body-segment being monitored. The pelvis is of particular interest because its proximity to the subject's center of mass allows one use the 6-DOF data regarding the pelvis to derive information about the movement of the subject as a whole. If multiple segments are monitored simultaneously, then the computations discussed below are carried out simultaneously and independently for each segment. However, the computations provided here are analogous for any body-segment to which the invention is applied, and, given the equations and computational steps described below, one of ordinary skill in the art of computer programming will be readily able to implement the invention with respect to any body-segment, or any combination of body-segments. Because of the complexity of the calculations, an embodiment in which computational duties are divided between a local processor and a remote processor, such as shown in FIG. 6 and discussed above, is preferred.

It is assumed, for basic mathematical modeling purposes, that all accelerometer modules are mounted firmly on the pelvis and thus define a rigid body. That is, the positions of, and therefore distances between, sensor modules are assumed to remain constant, and the different modules are assumed to maintain fixed orientations relative to one another. In the 6-DOF analysis of multiple segments, each segment is assumed to be a rigid body, and the subject is viewed as an aggregation of n rigid bodies, where n is the number of segments being monitored. Deviations from the rigid body assumption introduce error into the results, but that error is minimized or eliminated by the computational methods disclosed herein.

In the equations presented herein, the following conventions are used: 1) the three biaxial accelerometer modules designated as 206, 208, and 210 in FIG. 2 are arbitrarily referred to as upper-case "C," "A," and "B", respectively, in the superscripts and subscripts of the terms of the equations; 2) a dot over a variable implies differentiation with respect to time (e.g., $$\dot{r} = \frac{dr}{dt} \quad \text{and} \quad \ddot{r} = \frac{d^2 r}{dt^2};$$

3) 'x' is the cross product operator defined such that if $\underline{a}=a_x\underline{i}+a_y\underline{j}+a_z\underline{k}$ and $\underline{b}=b_x\underline{i}+b_y\underline{j}+b_z\underline{k}$, where $\underline{i}$, $\underline{j}$, and $\underline{k}$ are unit vectors oriented parallel to the x, y, and z axes respectively, then:

$$\underline{a} \times \underline{b} = (a_y b_z - a_z b_y)\underline{i} + (a_z b_x - a_x b_z)\underline{j} + (a_x b_y - a_y b_x)\underline{k}.$$

Because of the foregoing assumption that the body-segment (pelvis) represents a rigid body, there exists a well-defined angular velocity vector, $\underline{\omega}$, that characterizes the instantaneous rotational motion of the pelvis. The absolute velocity (relative to the earth) of any point on the pelvis can therefore be separated into translational and rotational terms, $$\dot{r}'_{total} = \dot{R}' + \underline{\omega}' \times \underline{r}' \qquad (1)$$

in which $\dot{R}'$ is the translational velocity of the pelvis (more precisely, the velocity of the geometrical center of the accelerometer module triad comprising 206, 208, 210), and $\underline{r}'$ is the position vector of the point relative to the Geometrical center. (In particular, $$\underline{r}_B = \left(\frac{h}{3}, \frac{b}{2}, 0\right)^T, \underline{r}_A = \left(\frac{h}{3}, -\frac{b}{2}, 0\right)^T \text{ and } \underline{r}_C = \left(-\frac{2h}{3}, 0, 0\right)^T$$

In Eq. 1, the primed notation indicates vectors whose components are relative to a fixed, inertial reference-frame (i.e., fixed to the earth), whereas unprimed vectors are measured relative to a non-inertial, anatomical reference-frame. The two frames of reference will henceforth be denoted as F' and F, respectively.

Differentiating Eq. 1 with respect to time furnishes an equation for the acceleration of points on the pelvis:

$$\ddot{r}'_{total} = \ddot{R}' + \dot{\underline{\omega}}' \times \underline{r}' + \underline{\omega}' \times \dot{\underline{r}}' = \ddot{R}' + \dot{\underline{\omega}}' \times \underline{r}' + \underline{\omega}' \times (\underline{\omega}' \times \underline{r}') \qquad (2)$$

Eq. 2 is fundamentally important for kinematic reconstruction. It indicates that it is possible, in principle, to solve for the translational acceleration, $\ddot{R}'$, and angular acceleration, $\dot{\omega}'$, (a total of six unknowns) if sufficiently many independent acceleration data channels are available. Integration of $\ddot{R}'$ and $\dot{\omega}'$ respectively provide the translational and angular velocities as functions of time. Integration a second time yields the translational positions and angular orientations.

To be able to employ Eq. 2 in practice, however, it is necessary to relate the acquired accelerometer measurements to the absolute acceleration, $\ddot{r}'_{total}$. Consider, for example, the output, $\underline{a}_A$, which is a two-component vector in the case of a biaxial accelerometer and is related to the absolute point acceleration of the module via an equation of the form:

$$\underline{a}_A = S_A T(\ddot{r}'_{total} + g\underline{k}') = S_A(T\ddot{r}'_{total} + gT\underline{k}') = S_A(\ddot{r}_{total} + gT\underline{k}') \qquad (3)$$

in which g is the acceleration due to gravity, $\underline{k}'$ is the unit vector in F' pointing downward (in the direction of gravity), and T is the time-varying transformation matrix from the inertial (earth-fixed) coordinate frame, F', to the (non-inertial) anatomical frame, F. That is, if $\ddot{r}'_{total}$ is the vector of acceleration components measured relative to the coordinate axes of F', the vector $\ddot{r}_{total} = T\ddot{r}'_{total}$ indicates the same physical acceleration, but with components measured relative to the instantaneous coordinate axes of F. $S_A$ is a 2×3 matrix that indicates the orientation of the sensitive axes of accelerometer module A relative to the pelvis. Its components are the direction cosines between the sensitive axes of module A and the coordinate axes of the anatomical reference-frame. If the modules are fastened firmly on the pelvis, the components of $S_A$ (unlike those of T) remain constant in time.

Combining Eqs. 2 and 3 yields the set of equations:

$$\underline{a}_A = S_A T[\ddot{R} + \dot{\underline{\omega}} \times \underline{r}_A + \underline{\omega} \times (\underline{\omega} \times \underline{r}_A) \times gT\underline{k}'] \qquad (4)$$

$$\underline{a}_B = S_B T[\ddot{R} + \dot{\underline{\omega}} \times \underline{r}_B + \underline{\omega} \times (\underline{\omega} \times \underline{r}_B) \times gT\underline{k}'] \qquad (5)$$

$$\underline{a}_C = S_C T[\ddot{R} + \dot{\underline{\omega}} \times \underline{r}_C + \underline{\omega} \times (\underline{\omega} \times \underline{r}_C) \times gT\underline{k}'] \qquad (6)$$

which can be written in a more compact form as:

$$\underline{a} \equiv \begin{pmatrix} \underline{a}_A \\ \underline{a}_B \\ \underline{a}_C \end{pmatrix} = H_1(\ddot{R} + gT\underline{k}') + H_2\dot{\underline{\omega}} + Q\underline{\omega}^2 \qquad (7)$$

$H_1$, $H_2$, and Q are constant matrices of size 6×3, 6×3, and 6×6, respectively. $\underline{\omega}^2$ denotes the 6×1 vector of quadratic angular velocity products, viz., $$\underline{\omega}^2 \equiv (\omega_x^2, \omega_y^2, \omega_z^2, \omega_x \omega_y, \omega_y \omega_z, \omega_x \omega_z)^T \qquad (8)$$

The elements of $H_1$ involve only the elements of $S_A$, $S_B$, and $S_C$ and therefore depend only on the accelerometer orientations. The elements of $H_2$ are sensitive to the distances between the accelerometer modules as well as their angular orientations. The same is true of Q.

1. Reconstruction of Angular Motion

Eqs. 4–7 constitute a system of differential equations involving both the translational and rotational accelerations. It is possible to isolate the rotational motion, however, by left-multiplying both sides of Eq. 7 by a 3×6 matrix, denoted as $N_1$, the rows of which comprise a basis for the left kernel space of $H_1$:

$$N_1 H_1 = 0 \tag{9}$$

It then follows that $$N_1 \underline{a} = N_1 [H_1(\ddot{R}+gT\underline{k}')+H_2\dot{\omega}+Q\omega^2] = N_1 H_2 \dot{\omega} + N_1 Q \omega^2 \tag{10}$$

Eq. 10 is a substantial simplification from Eq. 7 in that the translational accelerations and gravity dependence have been completely excluded.

2. Reconstruction of Translational Motion

The translational motion cannot be completely decoupled from the rotational motion, but an equation analogous to Eq. 10 can be derived for those cases in which the accelerometer modules are suitably arranged, as in FIG. 3. This is achieved by left-multiplying both sides of Eq. 7 by a 3×6 matrix, denoted as $N_2$, whose rows form bases for the kernel spaces of $H_1$ and Q:

$$N_2 \underline{a} = N_2 [H_1(\ddot{R}+gT\underline{k}')+H_2\dot{\omega}+Q\omega^2] = N_2 H_1 (\ddot{R}+gT\underline{k}') \tag{11}$$

where $N_2 H_2 = 0$ and $N_2 Q = 0$. Then, $$\ddot{R}+gT\underline{k}' = (N_2 H_1)^+ N_2 \underline{a} \tag{12}$$

in which superscript '+' denotes the (Moore-Penrose) pseudo-inverse of a matrix described by Campbell S L. Meyer C D Jr. *Generalized Inverses of Linear Transformations*, 1979, (Pitman: London. UK) It is necessary, in general, to use the pseudo-inverse because $N_2 H_1$ may be singular and thus not possess an inverse in the usual sense.

The translational motion is not completely independent of the rotational motion in that Eq. 12 yields not the pelvic accelerations in the inertial frame, $\ddot{R}'$, but the sum of the acceleration of the pelvis with the gravity term, $\ddot{R}+gT\underline{k}'$, in terms of the anatomical coordinate system, which is dependent on the angular position of the body by virtue of the transformation matrix, T. In some cases, this dependence may be ignored. For example, when the subject is walking upright, the anatomical z-axis and the earth-fixed z-axis nearly coincide, i.e., $T\underline{k}' \approx (0\ 0\ 1)^T = \underline{k}$ at all times during this motion, and so the vertical component of the pelvic accelerations with respect to the inertial coordinate frame, $\ddot{R}'=T^{-1}\ddot{R}$, may be approximated by the vertical component of $\ddot{R}$. In general scenarios, however, in which the orientation of the pelvis can be arbitrary, it is necessary to integrate Eqs. 10 and 11 together to obtain the angular positions, using the techniques described in the next subsection.

3. Deriving Pelvic Movement Information from 6-DOF Data

It is well-known from classical mechanics that the orientation of coordinate axes affixed to a rigid body with respect a set of inertial coordinate axes (and thus the aforementioned transformation matrix, T) can be characterized using three Euler angles, $\psi$ (yaw), $\theta$ (pitch or inclination), and $\phi$ (roll or bank). If the so-called "xyz convention" or "321 convention" is followed, the anatomical axes may be obtained from the inertial axes by first rotating through an angle $\psi$ about the inertial z-axis to produce an intermediate set of axes, then rotating through an angle $\theta$ about the intermediary x-axis to produce another intermediate set of axes, and finally rotating through an angle $\phi$ about the y-axis of this latter set of intermediate axes to yield the anatomical axes. The resulting transformation matrix, T, from the earth frame to the anatomical frame is given by:

$$T = \begin{bmatrix} \cos\theta\cos\Psi & \cos\theta\sin\Psi & -\sin\theta \\ \sin\phi\sin\theta\cos\Psi - \cos\phi\sin\Psi & \sin\phi\sin\theta\sin\Psi + \cos\phi\cos\Psi & \sin\phi\cos\theta \\ \cos\phi\sin\theta\cos\Psi + \sin\phi\sin\Psi & \cos\phi\sin\theta\sin\Psi - \sin\phi\cos\Psi & \cos\phi\cos\theta \end{bmatrix} \tag{13}$$

(Note that these finite rotations—unlike infinitesimal rotations—do not commute, which means that the order of the rotations in Eq. 13 is important.) The parameterization of this transformation by the Euler angles is useful for visualization of the corresponding motion, but the Euler angles are not as well-suited for computations because the repeated evaluation of trigonometric functions during numerical integration is costly, and the parametrization has singularities that must be avoided.

In order to avoid these problems we introduce the four Euler parameters, which yield a more efficient computational scheme, even though the number of variables is increased by one:

$$e_0 = +\cos\frac{\psi}{2}\cos\frac{\theta}{2}\cos\frac{\phi}{2} + \sin\frac{\psi}{2}\sin\frac{\theta}{2}\sin\frac{\phi}{2} \tag{14}$$

$$e_1 = +\cos\frac{\psi}{2}\cos\frac{\theta}{2}\sin\frac{\phi}{2} - \sin\frac{\psi}{2}\sin\frac{\theta}{2}\cos\frac{\phi}{2}$$

$$e_2 = +\cos\frac{\psi}{2}\sin\frac{\theta}{2}\cos\frac{\phi}{2} + \sin\frac{\psi}{2}\cos\frac{\theta}{2}\sin\frac{\phi}{2}$$

$$e_3 = -\cos\frac{\psi}{2}\sin\frac{\theta}{2}\sin\frac{\phi}{2} + \sin\frac{\psi}{2}\cos\frac{\theta}{2}\cos\frac{\phi}{2}$$

The inverse transformation between the two sets of variables is given by:

$$\theta = \sin^{-1}[-2(e_1 e_3 - e_0 e_2)] \tag{15}$$

$$\psi = \tan^{-1}\left[\frac{2(e_1 e_2 + e_0 e_3)}{(e_0^2 + e_1^2 - e_2^2 - e_3^2)}\right] \tag{16}$$

$$\phi = \tan^{-1}\left[\frac{2(e_0 e_1 + e_2 e_3)}{(e_0^2 + e_3^2 - e_1^2 - e_2^2)}\right] \tag{17}$$

The angular velocity components in the anatomical frame, F, are related to the derivatives of the Euler parameters via the equations:

$$\dot{e}_0 = -\frac{1}{2}(e_1\omega_x + e_2\omega_y + e_3\omega_z) \tag{18}$$

$$\dot{e}_1 = +\frac{1}{2}(e_0\omega_x + e_2\omega_z - e_3\omega_y)$$

$$\dot{e}_2 = +\frac{1}{2}(e_0\omega_y + e_3\omega_x - e_1\omega_z)$$

$$\dot{e}_3 = +\frac{1}{2}(e_0\omega_z + e_1\omega_y + e_2\omega_x)$$

In terms of the Euler parameters, the transformation $T$ becomes (see ANSI/AIM, *Atmospheic and Space Flight Vehicle Coordinate Systems* ANSI/AIM R-004-1992. February 1992.):

$$T = \begin{bmatrix} (e_0^2 + e_1^2 - e_2^2 - e_3^2) & 2(e_1 e_2 + e_0 e_3) & 2(e_1 e_3 - e_0 e_2) \\ 2(e_1 e_2 - e_0 e_3) & (e_0^2 + e_2^2 - e_1^2 - e_3^2) & 2(e_2 e_3 + e_0 e_1) \\ 2(e_1 e_3 + e_0 e_2) & 2(e_2 e_3 - e_0 e_1) & (e_0^2 + e_3^2 - e_1^2 - e_2^2) \end{bmatrix} \quad (19)$$

Thus, we can solve for the position of the pelvis as a function of time in several steps: first the system of differential equations in Eq. 10 can be integrated to find the angular velocity vector $\underline{\omega}$; then the system of Eqs. 18 can be integrated to obtain the four Euler parameters, and then T, via Eq. 19; and finally, Eq. 12 or Eqs. 4–6 can be integrated to obtain the translational motion of the pelvis, thereby completing the determination of every aspect of the motion. Note that, in practice, the inhomogeneous term $\underline{a}$ is only known at certain discrete times, so the integration must be performed using an interpolatory method, rather than a conventional technique that requires direct evaluations of $\underline{a}$ at arbitrary time steps.

4. Technique for Manually Calibrating Accelerometer Modules

It is to be emphasized that the application of 6-DOF technology to monitoring the movements of living subjects is distinguished from, and significantly more difficult than, the use of 6-DOF technology to monitor the motions of inanimate bodies, such as vehicles. Even where mathematical models assuming that the pelvis acts as a rigid body can be exploited, the reality is that, unlike inert bodies, accelerometer modules cannot be soldered to living subjects. Consequently, a major hurdle overcome by the present invention in applying 6-DOF technology to living subjects is the imprecise a priori alignment of the axes of measurement of the accelerometer modules relevant to the reference-frames, and inevitable and uncontrollable movements of the axes of measurement of the accelerometer modules relative to one another and to the reference-frames. To overcome this problem it is necessary to calibrate the accelerometer modules in order to establish, and re-establish, as necessary, the relationship between the axes of measurement and the axes of the inertial and anatomical reference-frames, as well as the position and orientation of the accelerometer modules with respect to the anatomical reference-frame. This information can then be used to correct for deviations in the orientations of the axes of measurement of the accelerometer modules.

One way to do this is what is referred to herein as "manual calibration." To accomplish this, the subject sequentially assumes and holds several different stances for short periods of time (e.g., ~30 sec). Each of the stances must be sufficiently distinct from one another so that there are appreciable differences in the accelerations measured by the suite of accelerometer modules in the various poses. The accelerometer data collected during each pose are averaged to minimize the effects of noise and involuntary movements. In principle, a great many different poses are suitable for calibration purposes, but we have found three particular poses to be ideal: lying supine, lying on the right side, and standing upright. If these positions cause difficulties for particular subjects, alternative poses can be used (e.g., with one or two hands in contact with a wall, leaning forward, leaning to the left, and leaning to the right).

During these static poses, the accelerometer modules measure only the gravity vector, $$\underline{a}_A = g S_A T \underline{k}' \quad \underline{a}_B = g S_B T \underline{k}' \quad \underline{a}_C = g S_C T \underline{k}' \quad (20)$$

For each calibration pose, a total of six data points are obtained, representing the median output level of each sensitive axis over the time during which the pose is held. It is assumed that $S_A$, $S_B$ and $S_C$ are constant across the various poses, which is tantamount to assuming that the shape of the attachment band (and thus the relative orientations between sensor modules) does not change between poses.

At the beginning of a sequence of calibration poses, $S_A$, $S_B$, and $S_C$ are known approximately, but not exactly. The same is true of T, which indicates the orientation of the pelvis (or rather the waistband 302) relative to the ground. If the subject assumes the three aforementioned calibration poses (lying supine, denoted by superscript '1'; lying on the right side, associated with superscript '2'; and standing upright, represented by superscript '3') exactly, then:

$$g T \underline{k}^{(1)} = g \underline{k}^{(1)} = (-g, 0, 0)^T \quad g T \underline{k}^{(2)} = g \underline{k}^{(2)} = (0, g, 0)^T \quad g T \underline{k}^{(3)} = g \underline{k}^{(3)} = (0, 0, g)^T \quad (21)$$

However, it is unlikely that the subject will perfectly assume the poses, and so a transformation of the form of Eq. 19 must be introduced for each calibration pose to represent the actual change in orientation from the idealized pose. The 12 Euler parameters representing these pose errors must then be found, along with the 18 independent components of $S_A$, $S_B$, and $S_C$, as those values which minimize the discrepancy between the predicted and observed accelerations. The calculations can be made independently for each accelerometer, and the three different sets of values for the 12 pose-error Euler parameters that are obtained while determining $S_A$, $S_B$, and $S_C$ can be compared and averaged, if accuracy is a priority. Alternatively, if a reduction in the number and complexity of calculations is more important, one of the calculations can be made in order to obtain both the 12 pose-error Euler parameters and either $S_A$, $S_B$, or $S_C$. The Euler parameters found during this first minimization can then be used for the second and third minimizations so that only the two remaining module orientation matrices need to be determined. This nesting of the minimization problems is made easier by the fact that, given the pose-error Euler parameters, a module orientation matrix can readily be determined from the observed accelerations by computing the polar decomposition of a certain auxiliary matrix (Fan K. Hoffman A J. "Some metric inequalities in the space of matrices." *Proc Amer Math Soc.* 1955: 6:111–116.). This sub-problem is known in statistical factor analysis as the problem of finding a "Procrustean transformation." This transformation makes it possible to solve the calibration problem indirectly as an unconstrained minimization problem, rather than viewing it as a nonlinear least-squares problem, subject to the constraints that $S_A$, $S_B$, and $S_C$ must be orthogonal matrices, in which case their inverses and transposes are equal:

$$S_A^{-1} = S_A^T \quad S_B^{-1} = S_B^T \quad S_C^{-1} = S_C^T \quad (22)$$

A number of specialized algorithms exist for such constrained problems Bjorck A. *Numerical Methods for Least Squares Problems.* 1996. (SIAM Pub: Philadelphia): Elden L. "Solving quadratically constrained least squares Problems using a differential-geometric approach." *BIT.* 2002; 42(2):323–335.; Elden L. "Algorithms for the regularization of ill-conditioned least squares problems." *BIT.* 1977; 17:134–145: Gander. W. "Least squares with a quadratic constraint," *Numer Math.* 1981; 36:291–307.), but it is usually easier to solve such problems in the absence of constraints, especially nonlinear constraints, such as the quadratic constraints in Eqs. 22. The unconstrained methods can be divided into two classes: (1) those that require computation of the derivatives of the function to be minimized with respect to the Euler parameters and the components of the module orientation matrices; and (2) "direct search" algorithms that do not require evaluation of these derivatives. In general, direct search algorithms are more robust and easier to implement than methods requiring derivatives, but are slower to converge and less accurate. Those skilled in the art will, without undue experimentation, be able to resolve the foregoing trade-offs by judicious selection of a standard algorithm that best suits their needs.

The correction factor thus obtained is then used to correct the 6-DOF data so that they more accurately reflect movements with respect to the anatomical reference-frame.

5. Technique for Adaptively Calibrating Accelerometer Modules

A more powerful and useful method of calibrating the system is to periodically recalibrate each accelerometer during the monitoring period. This technique, referred to herein as "adaptive calibration," is particularly helpful in monitoring body-segments that constantly change their orientation in real time with respect to gravity. Adaptive calibration has the very significant advantage of being a means of carrying out real time re-calibration of the accelerometer modules to correct for movement of the modules during the monitoring period.

At any given instant of time, the following relationship between the measured accelerations from a particular accelerometer, $\underline{a}$, and the components of these accelerations in the fixed inertial coordinate system, $\ddot{r}'$, exists:

$$\underline{a} = S\ T(\ddot{r}'+g\underline{k}') = P(\ddot{r}'+g\underline{k}') \quad (23)$$

The objective of adaptive calibration is to estimate the unknown, time-varying components of the orthogonal transformation matrix P, and the unknown $\ddot{r}'$, given a vector of acceleration measurements a over an interval of time. For the present purposes, the transformation that maps the fixed inertial coordinates into the anatomical coordinate axes, T, can be lumped together with the transformation that maps the anatomical coordinate axes into the accelerometer channel axes, S. The problem is under-determined, with more unknowns than equations. However, similar problems in other contexts have been successfully addressed by the use of modern sequential system identification techniques. We are aided in this effort by the fact that gravity is known, and by the fact that P is orthogonal, and has a convenient parameterization via the introduction of Euler parameters, as in Eq. 19.

A basic framework for the solution of the adaptive calibration problem is provided by a family of identification techniques known as recursive prediction-error methods (RPEM) Ljung, L. *System Identification: Theory for the User.* 2nd ed. 1999. (Prentice Hall: Englewood Cliffs, N.J.). In these methods, an initial guess at the unknown parameters is used to compute a prediction of the model one time step ahead, and then, advancing in time, the actual value is measured and compared to the predicted value. The guess at the unknown parameters is then refined by means of a nonlinear optimization algorithm that adjusts the values of the parameters in order to minimize the size of the error, while still satisfying the constraints imposed on the parameters. Then, using the updated parameter values an the estimate for the next time step, the process is repeated. These techniques may be tailored for particular problems by pre-filtering the errors before applying the optimization algorithm, choosing an appropriate measure of the size of the error, selecting an optimization algorithm with desirable properties, changing the extent to which the optimization algorithm is allowed to converge before advancing in time, and by using weighted combinations of the errors at several different times as an objective function. In addition, some strategies for global convergence may be implemented to ensure that the process is robust with respect to poor initial guesses Bliek, C H. Spelucci P. Vicente L N, Neumaier A, Granvilliers L, Monfroy E, Benhamou F, Huens E, Van Hentenryck P, Sam-Haroud D, Faltinas B. "Algorithms for Solving Nonlinear Constrained and Optimization Problems: The State of the Art." *COCONUT* Project Report, 2001.). For the problem at hand, the following procedure is proposed:

(a) At time $t_0$, initial guesses for $e_0$, $e_1$, $e_2$, $e_3$, and $\ddot{r}'$ are made. These trial values will be denoted by carets: e.g., the guess at $e_0$ is $\hat{e}_0$. An estimate $\hat{P}$ for P is then computed, using a parameterization of the form used in Eq. 19 for T.

(b) The error $$\underline{\varepsilon}(t_0) = \underline{a}(t_0) - \hat{P}(t_0)[\hat{\ddot{r}}'(t_0) + g\underline{k}'] \quad (24)$$

is then computed.

Next, the quantity $$\frac{1}{2}\underline{\varepsilon}(t_0)^T\underline{\varepsilon}(t_0) \quad (25)$$

is minimized by varying $e_0$, $e_1$, $e_2$, $e_3$, and $\ddot{r}'$ in accordance with a Newton-Gauss method (or another nonlinear least-squares algorithm) Nocedal J. Wright S J. *Numerical Optimization,* 1999. (Springer-Verlag: New York) to obtain the optimal parameter estimate at time $t_0$.

(d) The algorithm then proceeds to the next sample time, in the manner described above.

In this manner the 6-DOF data are repeatedly corrected during the period of monitoring. An analysis of the convergence of such algorithms can be found in Ljung L. Soderstrom T. *Theory and Practice of Recursive Identification.* 1983. (MIT Press: Cambridge, Mass.). It is anticipated that a suitably modified algorithm will yield good results. The problem formulation can also be changed to incorporate the measurements of all of the accelerometer modules, rather than a single accelerometer, and this would improve the quality of the parameter estimate, at the expense of solving a larger minimization problem at each time step. Since these calculations can be carried out by remote processor 620, maximizing accuracy, not minimizing computational time, is possible.

6. Smoothing of the Accelerometer Outputs

One of the main problems that must be overcome when using accelerometer modules is the presence of sensor noise. Such noise can lead to a growth in time of the variances of estimators of integrated quantities (e.g., velocity and orientation), and make it difficult to calculate such variables accurately with increasing time span. Without using information from other sensors, a systematic acquisition of new initial conditions and frequent restarting of any integration of the equations of motion from these initial conditions is the only way to ensure reasonable accuracy. However, noise problems may be ameliorated by the introduction of judiciously chosen filters or smoothers, such as a spline smoother applied to the accelerometer outputs. Such a smoother fits a sequence of piecewise-smooth cubic polynomials to the sampled accelerations $a_i$=1 . . . , n in such a way that the resulting spline s(t) minimizes the quantity:

$$\sum_{i=1}^{n} \{a_i - s(t_i)\}^2 + \xi \int_0^t \{s''(x)\}^2 dx \qquad (26)$$

The first-term is the residual sum-of-squares, which represents the bias of the spline fit, and the second term, which is multiplied by the positive parameter $\xi$, is a "roughness penalty" related to the variance of the estimate. The spline, then, is a compromise between goodness of-fit and smoothness, as regulated by $\xi$. This important smoothing parameter is also called the "bandwidth" of the smoother, because of its analogous role in the roughly equivalent method of kernel, or moving-average smoothers. The selection of $\xi$ can be automated: for example, it can be chosen to be a number that furnishes a local minimum of the Generalized Cross-Validation (GCV) score of Craven P. Wahba G. "Smoothing noisy data with spline functions." *Numerische Mathematik*, 1979; 31:377–403., a widely-used statistical criterion:

$$GCV(\xi) = \frac{\left\{\sum_{i=1}^{n} a_i - s(t)\right\}^2}{\{n - trace\,[A(\xi)]\}^2} \qquad (27)$$

where $A(\xi)$ is the so-called "hat matrix" relating the value-second derivative representation of the spline coefficients to the sampled accelerations, $\underline{s}=A(\xi)\underline{a}$. Although not appropriate for every application, this choice of bandwidth furnishes a starting point from which a more detailed investigation of the proper amount of smoothing can be made. Some considerations involved in conducting such an investigation are discussed in Loader C, *Local Regression and Likelihood*. 1999, (Springer-Verlag: New York). The resulting smoother can be computed by means of the algorithm of Woltring, which is an implementation of the fast GCV algorithm of Hutchinson and de Hoog Hutchinson M F, de Hoog F R. "Smoothing noisy data with spline functions." *Numerische Mathematik*, 1985: 47(1); 99–106.). Such smoothers have been found to be asymptotically optimal among nonparametric models, with only mild increases in bias at the boundaries 0 and t, and they preserve many fine variations in the original data. The spline smoother can be computed in "linear time," and so it can even be used in "on-line" applications, although this is not required in embodiments employing remote unit processing capabilities. Furthermore, it can be used in circumstances where there is no useful characterization of the frequency band in which noise is present, or when noise has contaminated a wide range of frequencies through aliasing.

F. Applications of 6-DOF Data for Monitoring Subjects—[FIGS. 7–9]

Having acquired 6-DOF data regarding a subject, it is possible to exploit those data to obtain information about the subject's movements, position, and orientation. In addition, certain types of functional information regarding the subject may be derived from the 6-DOF data, as described below.

1. Acquiring Information Descriptive of Sudden Movements from 6-DOF Data.

In this section a brief overview is provided of the techniques for obtaining subject-movement information relative sudden movements indicative of falls and near-fall events. Such information includes detecting falls, discriminating falls from other activities, and estimating fall directionality. Approaches based on the automated recognition of patterns in the acceleration history to detect and discriminate falls have been most amenable to 6-DOF data analysis. Criteria based on the tipping of the pelvis enable simple characterization of fall events. Such techniques do not require integration of the equations of motion, but rely instead on approximations that are valid under restricted circumstances.

Discriminating falls from other sudden movements is achieved by identifying features in the acceleration history that can serve as a means of differentiating falls from other kinds of potentially confounding activities. Obvious distinguishing features of the acceleration history of a fall are the large peaks in acceleration observed immediately before (i.e., during "free fall," where the vertical acceleration approaches zero) and after impact with the ground. Although such accelerations nearly always occur during a fall, equally large peaks in acceleration can take place during other activities of daily living, such as skipping, jumping, running, and sitting, acceleration magnitude alone is not sufficient for identifying fall events. However, setting a threshold on the magnitude of the acceleration is a logical first step to isolate candidate fall events. (Similarly, setting a threshold on the free-fall time duration can also be useful in discriminating fall events from non-fall events. This criterion was incorporated indirectly into the fall detection algorithm, as is discussed below.) A typical acceleration history was obtained for a subject engaging in various types of activities—walking, running, skipping, flopping into a chair, ascending and descending, stairs, and falling onto a soft mat. Of this variety of activities, only running, skipping, and flopping into a chair produced acceleration magnitudes comparable to those observed during fall events. Hence, by judiciously choosing an acceleration threshold based on empirical data, and ignoring accelerations below this threshold, one excludes many types of common activities from consideration in seeking to identify fall events. Reliance upon the magnitude (rather than specific components) of the acceleration vector has the advantage of being robust with respect to calibration error (in terms of the exact orientation of the local unit positioned on the pelvis).

It then remains to distinguish falls from other activities that produce large peaks in acceleration magnitude. The best approach known for this purpose is based on an estimate of the power spectral density of a segment of the acceleration history computed around any peak in acceleration of a candidate fall event. This temporally-localized frequency-domain representation of the acceleration history may be rapidly and reliably computed, and contains much of the information found in the original signal. It has the added benefit that it is easier to state criteria for fall detection in the frequency domain, as problems with post-fall transients in the time domain are avoided.

A comparison of power spectral densities computed from similar-duration time-series data segments of fall and non-fall events for a typical subject reveals that there is a clear distinction between falls and other types of motions in the frequency domain. The running and skipping profiles have concentrations of power at higher frequencies corresponding to the cadence of the subject. In contrast, walking, stair-climbing (ascending and descending), sitting, and falling profiles all have peaks in power at low frequencies. However, fall events are clearly distinguishable from walking, stair climbing, and chair sitting based on the amplitude of the power spectral density at low frequencies. This makes intuitive sense in that the greater the amount of time spent in free fall (i.e., 0 g), the less will be the power at these low frequencies. (This follows from the fact that the power spectral density of a signal that is equal to zero—i.e., free fall acceleration—is also zero.) Time spent in free fall is, therefore, incorporated indirectly into the fall detection algorithm.

In summary, the current fall detection and discrimination algorithms are based on the use of a threshold in the acceleration magnitude, followed by a second threshold in the maximum power permitted in the low-frequency band, followed by a third threshold on the maximum power permitted at higher frequencies.

2. Determining Fall Directionality

The directionality of fall events is also of interest. An algorithm was therefore devised to estimate the tipping motions of the pelvis immediately before a fall, thereby avoiding the need for integration or precise calibration. The method used currently was derived by assuming a triad of accelerometer modules, A, B, and C, as shown in FIG. 2, each of which is assumed to be located at a vertex of an isosceles triangle formed by the anterior-superior iliac spine (separated by the length of the base, b) and sacrum (at a height h from the base). The sensitive axes of the accelerometer modules A, B, and C are ideally (but, in practice, are only approximately) aligned with the anatomical reference-frame 214. Assuming that the angular velocity is sufficiently small, so that terms that are second-order in the angular velocity $\omega$ are negligible in comparison to the angular accelerations $\dot{\omega}$, it can be shown that:

$$\dot{\omega}_x \approx \frac{a_{B,z} - a_{A,z}}{b} \quad \dot{\omega}_y \approx \frac{a_{C,z} - a_{A,z}}{h} \quad \dot{\omega}_z \approx \frac{a_{A,x} - a_{B,x}}{b} \quad (28)$$

where, for example, $\dot{\omega}_x$ refers to the angular acceleration about the body-fixed x axis, and $a_{A,y}$ is the acceleration measured by the case-axis of accelerometer A that is most closely aligned with the body-fixed taxis. With the aid of these approximations, the angular acceleration of the pelvis may be calculated when a subject wearing the local unit first begins to fall from a standing or sitting position. A simple sign criterion suffices to determine the quadrant into which the subject is falling:

| Quadrant I: | (0°→90°) | $\dot{\omega}_x > 0, \dot{\omega}_y < 0$ | [29a] |
| Quadrant II: | (90°→180°) | $\dot{\omega}_x < 0, \dot{\omega}_y < 0$ | [29b] |
| Quadrant III: | (180°→270°) | $\dot{\omega}_x < 0, \dot{\omega}_y > 0$ | [29c] |
| Quadrant IV: | (270°→360°) | $\dot{\omega}_x > 0, \dot{\omega}_y > 0$ | [29d] |

3. Monitoring Respiratory Function with Accelerometer Signals

Figure 7:
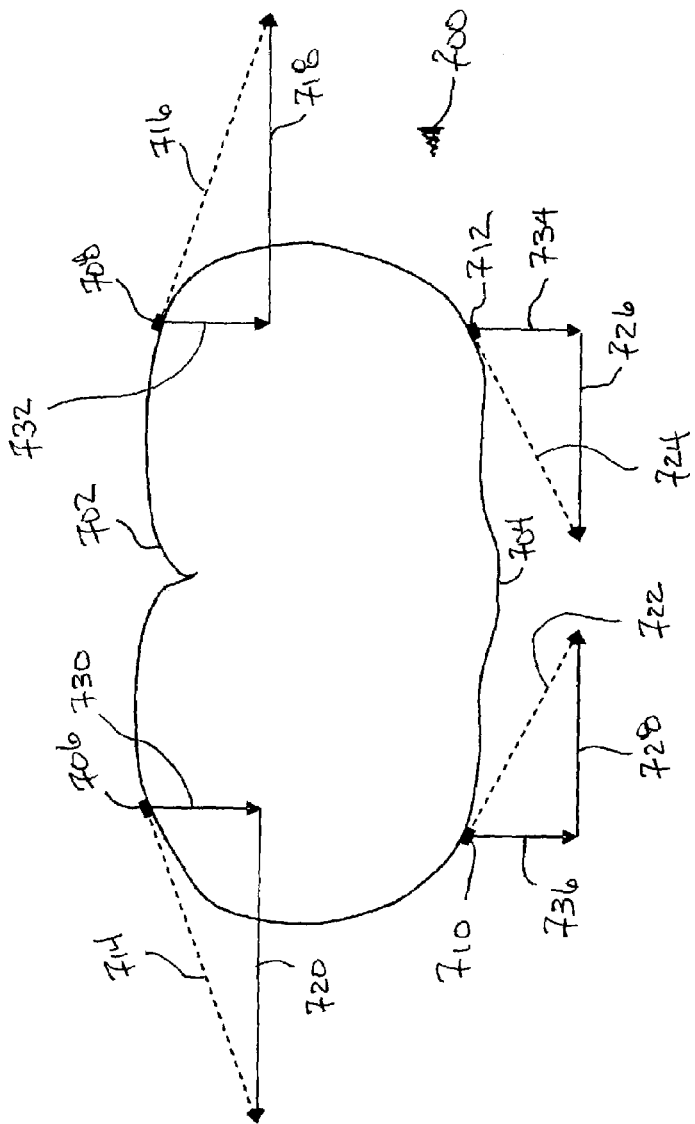
FIG. 7 represents a transverse section of a subject's pelvis showing the positions of accelerometer modules when used to acquire respiratory function data.

The technique of extracting information regarding respiratory function from an array of accelerometer modules worn on the pelvis can be better understood by referring to FIG. 7, which is a cross-section of a human pelvis at about the level of L5/S1, with four uniaxial accelerometer modules, 706, 708, 710, 712, attached. Extraction of respiratory function data is accomplished using a differential technique that segregates information regarding respiratory movements from "common-mode noise" (composed largely of pelvis accelerations that are not of interest).

The technique separates acceleration of the anterior aspect of the pelvis 704 from the posterior aspect 702. The fundamental premise of this approach is that respirations have a disproportionate affect on the anterior aspect of pelvic motion, which can be exploited using a differential technique. In particular, the isolation of a high signal-to-noise ratio respiratory signal is accomplished using an adaptive noise-cancellation algorithm that employs the least means square (LMS) filtering technique. Widrow B. Glover J R Jr, McCool J N, Kaunitz J, Williams CS, Hearn R H, Zeidler J R. Dona E Jr, Goodlin R C, "Adaptive noise canceling: principles and applications." *Proc IEEE*, December 1975; 63:1692–1716.) The approach treats the net acceleration in the summed (horizontal plane) anterior accelerometer channels as representing the signal of interest (i.e., acceleration due to respirations) plus noise, whereas the summed (horizontal plane) posterior accelerometer signal represents mainly noise, which is, however, highly correlated with the noise in the composite anterior accelerometer signal. The noise is due mainly to accelerations caused by motion of the pelvis in the transverse plane, such as during sway, walking, and running. Other noise, which is not correlated between the accelerometer modules, is largely accelerometer electronic noise, but this is relatively small in comparison to the "motion noise."

As shown in FIG. 7, even without calibration, the horizontal axis of each of the four accelerometer modules, which is located in the transverse plane of the pelvis, is composed of two components. (The vectors in FIG. 7 are meant to imply alignment with the active sensor axes and not actual motions.) With respect to the posterior accelerometers 706 and 708, one vector component 730 is oriented largely in the body-axis anterior-posterior direction, and a second vector component 720 is oriented in the medio-lateral direction. An identical relationship holds for vectors 732 and 718 with respect to accelerometer 708. If the outputs from accelerometer 706 and accelerometer 708 are summed, the medio-lateral components, being of opposite direction (and therefore signs) will largely cancel, with the resultant posterior vectors 730 and 732 being oriented largely in the anterior-posterior direction. Precise cancellation is not required; the goal is to obtain a signal that is oriented largely in the anterior-posterior direction. Similarly with respect to anterior accelerometer module 710, one vector component 736 is oriented in the anterior-posterior direction, and the other 728 in the medio-lateral direction. The same relationship obtains with respect to accelerometer 712 and vectors 734 and 726. If the outputs of anterior accelerometer modules 710 and 712 are summed, the medio-lateral components will again largely cancel, with the resultant vectors 734 and 736 being oriented again largely in the anterior-posterior direction. The sum of the two posterior accelerometer modules is taken here to represent the "motion noise" signal that is highly correlated with the "motion noise" signal in the anterior accelerometer modules. The fundamental concept of the LMS adaptive noise canceling technique is to exploit the second-order correlation between the two noise signals, $n_0$ and $n_1$, as shown in FIG. 8, to yield an output signal, ŝ, that is largely the signal of interest (i.e., respirations) without motion noise.

Figure 8:
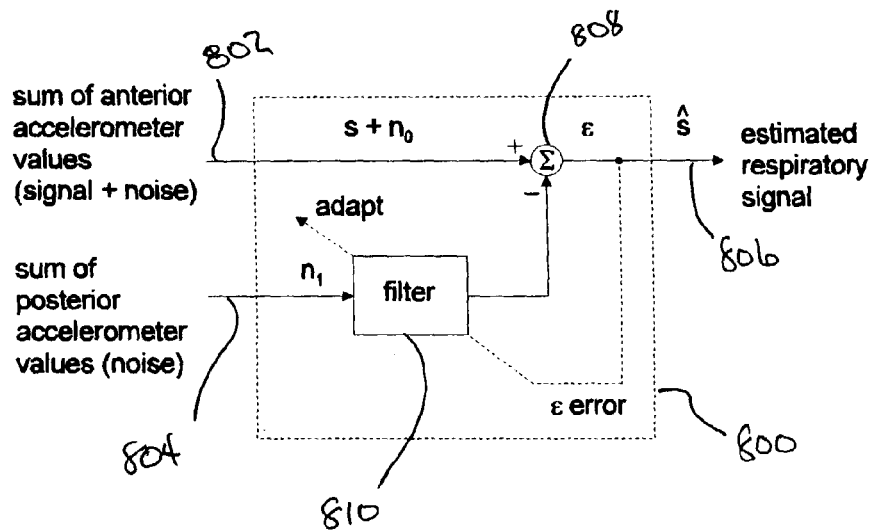
FIG. 8 is a block diagram illustrating the adaptive noise-cancelling concept used in acquiring respiratory function data.

Referring to FIG. 8, the LMS noise cancellation algorithm utilizes an adaptive linear transversal filter 810 to process the noise channel 804 and estimate the noise, $n_0$, in order to minimize the mean-squared error at the output of the summing junction 808 ($s+n_0-f(n_1)$), where $f(n_1)$ here is taken to be a nonlinear function of the noise signal $n_0$. (Although a linear filter is used to process the $n_1$ signal, the fact that its weights are adaptive makes the overall filter nonlinear.) The weights of the transversal filter are adapted via the LMS algorithm to minimize the output error, E, thereby effectively canceling the common-mode noise. In this way, the relatively small component of pelvic acceleration that is due to breathing, which would generally be obscured by the other motions of the body, can effectively be extracted. The resulting output 806 is a time-varying signal from which one can extract respiratory periods and breathing depth. Upon calibration, this information is converted to tidal rate and tidal volume.

The LMS algorithm is very efficient computationally, and has been successfully employed in a wide range of on-line and adaptive applications. The performance of the LMS technique in noise cancellation is also well-documented. Quirk K J, Milstein L B, Zeidler J R, "A performance bound for the LMS estimator." *IEEE Trans In form Theory*, May 2000 46; 1150–8.; Zeidler J R. "Performance analysis of LMS adaptive prediction filters." *Proc IEEE. Dec.* 1990; 78:1781–1806.)

4. Deriving Energy Expenditure Information from 6-DOF Data

Pilot experiments were undertaken to explore the invention's capabilities for estimating the expenditure of energy during physical activity from 6-DOF data. To date, we have conducted tests on fifteen individuals, including two children, six men, and seven women. Each test subject was instrumented with a local unit essentially as described in FIG. 3, a heart rate monitor, and a portable metabolic measurement (indirect calorimetry) system that also measured heart rate. The test protocol called for each subject to undergo a manual calibration routine, as described above, and then walk at a speed of 2.5 mph around an indoor track for ten minutes. Following a brief rest of two minutes, the subjects would then walk around the track at a pace of 3 mph for ten minutes. After another two-minute rest, the subjects would walk for a final ten minutes at a speed of 4 mph, and then perform a final manual calibration. Data were collected continually using the metabolic measurement system, and during the walking periods by the local unit. After post-processing by a processor of a remote unit, the data were subjected to neural network analysis in order to construct a preliminary regression model relating kinetic, heart rate, and metabolic quantities.

Specifically, a polynomial neural network was constructed to relate "kinetic energy counts" summed over a period of one minute and average heart rate to energy expenditure due to exercise over the same minute. A neural network is a type of nonparametric, nonlinear algorithm used for regression and modeling, wherein many simple approximative elements are combined in complex ways to provide a powerful and flexible model. (See 1994 Ward D. "Generalized networks for complex function modeling." *Proc. IEEE Syst Man & Cybemetics Conf* (*SMC*-94). October 2–5. 1994.) For this initial model, the resting metabolic rate was determined via the regression equations of Roza and Shizgal (Roza A M. Shizgal H M, "The Harris Benedict equation reevaluated: resting energy requirements and the body cell mass." *Am J Clin Nutr.* 1984 Jul; 40(1):168–82.). The protein component of the metabolism was neglected for the low intensity exercises carried out in the tests. The thermal equivalents of oxygen for the non-protein respiratory quotient were determined by interpolating the data of Zuntz (Zuntz H. *Pflugers Arch Physiol,* 1901; 83:557). The kinetic energy counts are given by $$AC_{KE} = \frac{1}{2}\{m(AC_{\ddot{r}_x} + AC_{\ddot{r}_y} + AC_{\ddot{r}_z}) + I_{yy}AC_{\dot{\omega}_y} + I_{zz}AC_{\dot{\omega}_z} + I_{xx}AC_{\dot{\omega}_x}\} \quad (30)$$

where $$AC_{\ddot{r}_x} = \sum_i |\ddot{r}_x(t_i)|$$

and the summation is taken over a certain designated time period, in this case one minute. The necessary mass moments of inertia ($I_{xx}$, etc.) were obtained from NASA Reference Publication 1024 (NASA Reference Publication 1024: *Anthropometric Source Book, Volume I: A Handbook of Anthropometric Data*, July 1978) because they are difficult to measure. The kinetic energy counts were introduced as a coarse approximation to the true kinetic energy of a rigid body, $$KE = \frac{1}{2}\{m(\dot{r}_x^2 + \dot{r}_y^2 + \dot{r}_z^2) + I_{xx}\omega_x^2 + I_{yy}\omega_y^2 + I_{zz}\omega_z^2\} \quad (31)$$

to avoid the need for integration.

Figure 9:
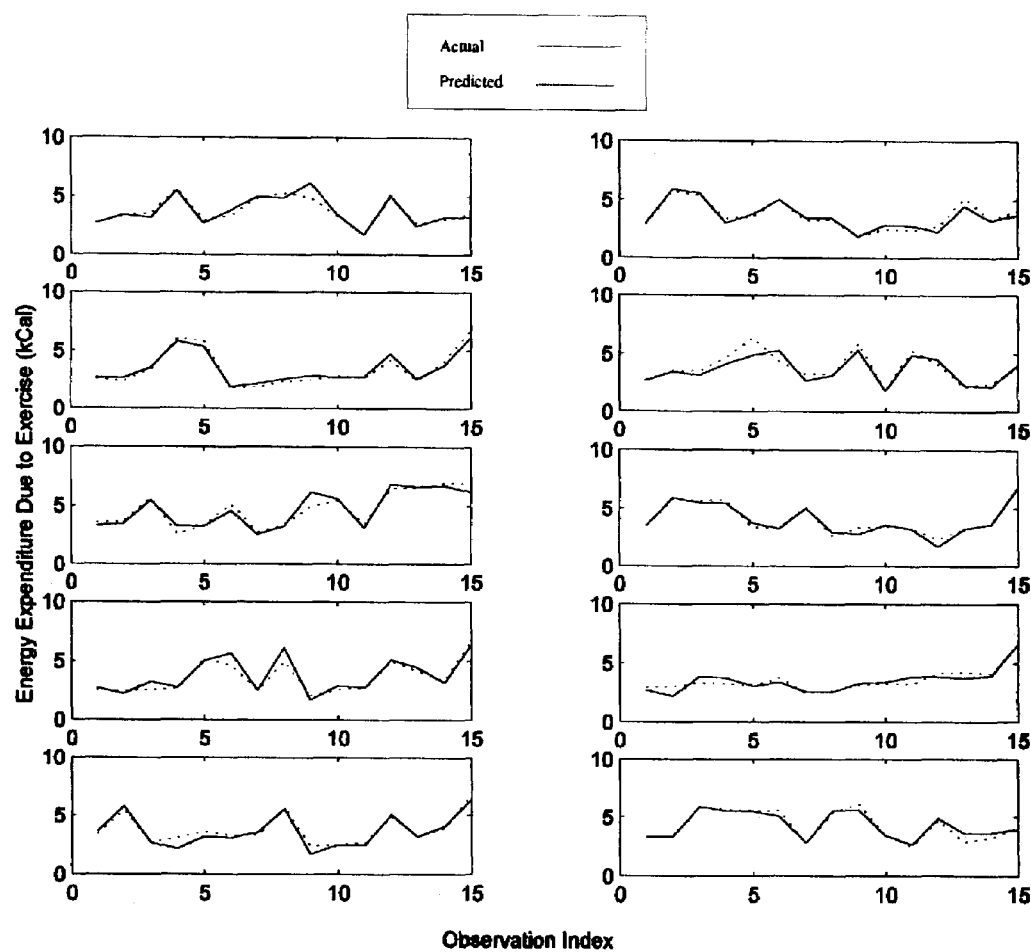
FIG. 9 represents the actual and predicted energy expenditure (based on data collected in 15 subjects) as determined by the method of the invention.

Despite the small number of observations in the pilot study, the neural networks had good predictive power when trained on a subset of the data and validated on the remainder. This was especially true when the excluded data represented randomly chosen observations from single tests, and was also true in some instances when the totality of observations for one individual were withheld from the training set. FIG. 9 and Table I support this contention.

Referring to FIG. 9, which presents the energy expenditure measured using a portable indirect calorimetry system compared to predicted energy expenditure values for ten individuals using the method discussed above. In each graph, the solid lines represent actual energy expenditure values for observations from data withheld from the training set for the neural network, and the dotted lines represent the predictions of that neural network for those observations. Note the close agreement in almost all cases.

Table I summarizes the statistical performance of a neural network analysis for which a random data record was withheld from training data. The $R^2$ statistic is the percent of the 1159 output variance accounted for by the model—a perfect model would have $R^2 \approx 1$—and the RMS Error is the root-mean-square of the error between the true and modeled outputs.

TABLE I

| Diagnostic | Case 1 | Case 2 | Case 3 | Case 4 | Case 5 | Case 6 | Case 7 | Case 8 | Case 9 | Case 10 |
|---|---|---|---|---|---|---|---|---|---|---|
| $R^2$ | 0.901 | 0.934 | 0.950 | 0.807 | 0.916 | 00.964 | 0.912 | 0.864 | 0.940 | 0.936 |
| RMS Error | 0.398 | 0.295 | 0.311 | 0.541 | 0.459 | 0.268 | 0.488 | 0.385 | 0.367 | 0.293 |

CONCLUSIONS, RAMIFICATIONS, AND SCOPE

From the foregoing, it will be appreciated that our invention represents a novel, useful, and non-obvious solution to the problems of 1) how to acquire 6-DOF data in living subjects; 2) how to utilize 6-DOF data to effectively monitor subjects' movements in three-dimensional space; and 3) how to combine and synchronize 6-DOF data with physiological data in order to more comprehensively monitor subjects. The foregoing examples and embodiments represent the best modes known to us for practicing the invention, but they do not represent the only modes. Therefore, it is to be understood that the present invention is not limited to the precise details of structure and function shown and set forth in this specification, for from the foregoing disclosures modifications will occur and be obvious to those skilled in the art. Thus, the scope of the invention is to be determined by the claims enumerated below, and their equivalents as the law so allows, rather than by any example herein provided.

We claim:

1. A method of monitoring a subject during a monitoring period, said method comprising the steps of:
   (a) attaching at least one array of accelerometer modules to at least one body-segment of the subject, the accelerometer modules having an aggregate of at least six axes of measurement;
   (b) positioning the subject in at least three substantially stationary calibration poses, the calibration poses being sufficiently different from one another to produce appreciable differences in acceleration signals produced by the array of step (a);
   (c) acquiring acceleration signals from the array of step (a) for each of the calibration poses of step (b), said acceleration signals representing the accelerations of the body-segment relative to each of the x, y, and z-axes of an anatomical reference frame;
   (d) averaging the acceleration signals acquired at step (c) to minimize the effects of noise and involuntary motion;
   (e) acquiring a gravity vector value from the averaged acceleration signals obtained at step (d);
   (f) applying the gravity vector value acquired at step (e) to the acceleration signals obtained at step (c) to obtain a correction factor for correcting the orientation of each axis of measurement relative to the anatomical reference-frame;
   (g) acquiring from the array of step (a) acceleration signals representing the accelerations of the body-segment movements relative to each of the x, y, and z—axes of an anatomical reference-frame;
   (h) processing the acceleration signals acquired at step (g) to obtain 6-DOF data;
   (i) processing the 6-DOF data obtained at step (h) by incorporating the correction factor obtained at step (f) to obtain information regarding the body-segment movement with respect to the x, y, and z-axes of an inertial reference-frame; and
   (j) displaying the body-segment movement information obtained at step (i).

2. The method of claim 1 further comprising adaptively calibrating the accelerometer modules using recursive prediction-error analysis by carrying out the steps of:
   (k) constructing a model of the subject's movements based on the 6-DOF data obtained at step (h);
   (l) guessing a value with respect to some chosen future point in time for at least one parameter used to construct the model;
   (m) measuring the value for the parameter when the future point in time arrives;
   (n) obtaining a correction factor by refining the guess made at step (k) with respect to a next future point in time and applying a nonlinear optimization algorithm that minimizes the size of the error between the value guessed at step (l) and value measured at step (m);
   (o) applying the correction factor obtained at step (n) to the 6-DOF data obtained in step (h), whereby the corrected 6-DOF data more accurately represent the movements of the body-segment with respect to the inertial reference-frame; and,
   (p) repeating steps (k) through (o) during the monitoring period.

3. A method of monitoring respiratory functions of a subject, said method comprising the steps of:
   (a) attaching an accelerometer array to the subject;
   (b) acquiring from the array of step (a) acceleration signals representative of the subject's respiratory movements; and,
   (c) processing the acceleration signals to segregate information representing the subject's respiratory functions from common-mode noise by applying a least mean squared (LMS) noise cancellation analysis whereby the common-mode noise contained in the acceleration signals is cancelled.

4. The method of claim 3 wherein the LMS noise cancellation analysis of step (c) further comprises utilizing a linear transversal filter to process the acceleration signals acquired at step (b).

5. The method of claim 3 wherein step (a) further comprises the steps of:
   (d) attaching at least two posterior accelerometers of said accelerometer array to the posterior side of the subject's body with the horizontal axis of each of the posterior accelerometers located in the transverse plane of the subject's body such that the summed outputs of said posterior accelerometers represent acceleration signals in which the medio-lateral components of the subject's movements are largely cancelled; and,
   (e) attaching at least two anterior accelerometers of said accelerometer array to the anterior side of subject's body with the horizontal axis of each of the anterior accelerometers located in the transverse plane of the subject's body such that the summed outputs of said anterior accelerometers represent acceleration signals in which the medio-lateral components of the subject's movements are largely cancelled.

6. The method of claim 5 further comprising the steps of:
   (f) summing the outputs of the anterior accelerometers attached at step (d);
   (g) summing the outputs of the posterior accelerometers attached at step (e); and,
   (h) processing the summed outputs of steps (f) and (g) according to step (c).

7. The method of claim 3 wherein the common-mode noise cancelled at step (c) comprises motion-noise.

8. A method of monitoring a subject during a monitoring period, comprising the steps of:
   (a) attaching at least one accelerometer module to at least one body-segment of the subject;
   (b) acquiring from the acceleration module attached at step (a) acceleration signals representing the accelerations of the body-segment relative to each of the x, y, and z-axes of an
   (c) processing the acceleration signals acquired at step (b) to obtain six degrees of freedom (627 DOF) body-segment movement information descriptive of the movements of the body segment with respect to each of the x, y, and z-axes of an inertial reference-frame;
   (d) acquiring at least one type of physiological data regarding the subject;
   (e) processing the physiological data acquired at step (d) to obtain physiological information regarding the subject;
   (f) synchronizing the 6-DOF body-segment movement information obtained at step (c) with the physiological information obtained at step (e) to obtain synchronized 6-DOF body-segment movement information and physiological information; and,
   (g) displaying said synchronized 6-DOF body-segment movement information and physiological information obtained at step (f) in at least one format comprehensible to humans.

9. The method of claim 7 further comprising the step of storing the 6-DOF synchronized body-segment movement information and physiological information obtained at step (f).

10. The method of claim 7 further comprising the step of transmitting the 6-DOF synchronized body-segment movement information and physiological information obtained at step (f) to at least one remote location.

11. A method of monitoring the respiratory functions of a subject, said method comprising the steps of:
   (a) attaching at least one accelerometer module to the posterior side of the subject's body such that the output of said posterior accelerometer module represents acceleration signals in which the posterior medio-lateral components of the subject's movements are largely cancelled;
   (b) attaching at least on anterior accelerometer module to the anterior side of subject's body such that the output of said anterior accelerometer module represents acceleration signals in which the anterior medio-lateral components of the subject's movements are largely cancelled;
   (c) acquiring the outputs of the posterior accelerometer module attached in step (a);
   (d) acquiring the outputs of the anterior accelerometer module attached at step (b); and,
   (e) processing the outputs acquired at step (c) and step (d) to segregate information representing the subject's respiratory movements from motion noise.

12. The method of claim 11 wherein step (e) is carried out by applying a least mean squared (LMS) noise cancellation analysis.

13. A method of monitoring respiratory functions of a subject, said method comprising the steps of:
   (a) acquiring acceleration signals from at least one accelerometer module attached to the subject;
   (b) processing the acceleration signals obtained at step (a) to obtain anterior-posterior acceleration signals representing anterior-posterior acceleration vectors largely free of medio-lateral acceleration vectors; and
   (c) extracting from the anterior-posterior acceleration signals obtained at step (b) an acceleration component that is due to breathing.

14. The method of claim 13 wherein step (c) comprises applying a LMS adaptive noise-cancellation technique.

15. A subject-monitoring system for monitoring the respiratory function of a subject during a monitoring period, said subject-monitor system comprising:
   (a) an accelerometer means that produces acceleration signals representing the movement of at least one of the subject's body segments relative to each of the x, y, and z-axes of a reference-frame;
   (b) attachment means for attaching said accelerometer means to the subject;
   (c) an acceleration signal processing means for processing the acceleration signals to yield movement data representative of the anterior-posterior components of the movements of the subject's body segment during the monitoring period; and
   (d) a data processing means for processing the movement data to segregate respiratory function information from motion noise.

* * * * *

UNITED STATES PATENT AND TRADEMARK OFFICE
CERTIFICATE OF CORRECTION

PATENT NO. : 6,997,882 B1  
APPLICATION NO. : 10/328214  
DATED : February 14, 2006  
INVENTOR(S) : B. Eugene Parker, Jr. et al.

Page 1 of 1

It is certified that error appears in the above-identified patent and that said Letters Patent is hereby corrected as shown below:

In the Specification

Column 3, line 58 Change 'by 6-DOF measurement' to -- from 6-DOF measurement --

Column 5, line 48 Change 'data over the some' to -- data over some --

Column 11, line 25 Change 'The HR electrodes 404 and 406 collect the data and HR electrode 402 acts as a reference.' to -- The HR electrodes 402 and 406 collect the data and HR electrode 404 acts as a reference. --

Column 21, line 40 Change 'measurements a over an interval' to -- measurements $\underline{a}$ over an interval --

Column 25, line 46 Change 'body-fixed taxis' to -- body-fixed y-axis --

Column 28, line 64 Change 'percent of the 1159 output variance' to -- percent of the output variance --

In the Claims

Column 31, line 17 Change 'z-axis of an' to -- z-axis of an anatomical reference frame; --

Column 31, line 19 Change 'freedom (627 DOF)' to -- freedom (6-DOF) --

Column 32, line 1 Change 'on anterior' to -- one anterior --

Signed and Sealed this  
Eighth Day of November, 2016

Michelle K. Lee  
*Director of the United States Patent and Trademark Office*

(12) INTER PARTES REVIEW CERTIFICATE (2029th)
United States Patent
Parker et al.

(10) Number: US 6,997,882 K1
(45) Certificate Issued: Apr. 19, 2021

(54) 6-DOF SUBJECT-MONITORING DEVICE AND METHOD

(75) Inventors: B. Eugene Parker; Brendan M. Fabeny; Edward C. Larson; Jeffrey F. Monaco

(73) Assignee: SMART WEARABLE TECHNOLOGIES, INC.

Trial Number:

IPR2018-00252 filed Nov. 28, 2017

Inter Partes Review Certificate for:

Patent No.: 6,997,882
Issued: Feb. 14, 2006
Appl. No.: 10/328,214
Filed: Dec. 21, 2002

The results of IPR2018-00252 are reflected in this inter partes review certificate under 35 U.S.C. 318(b).

INTER PARTES REVIEW CERTIFICATE
U.S. Patent 6,997,882 K1
Trial No. IPR2018-00252
Certificate Issued Apr. 19, 2021

AS A RESULT OF THE INTER PARTES REVIEW PROCEEDING, IT HAS BEEN DETERMINED THAT:

Claims 8-10 are disclaimed.

\* \* \* \* \*